(12) United States Patent
Fecher et al.

(10) Patent No.: US 7,714,132 B2
(45) Date of Patent: May 11, 2010

(54) TETRAHYDROPYRIDOINDOLE DERIVATIVES

(75) Inventors: Anja Fecher, Basel (DE); Heinz Fretz, Riehen (CH); Kurt Hilpert, Hofstetten (CH); Markus Riederer, Liestal (CH)

(73) Assignee: Actelion Pharmaceuticals, Ltd., Allschwil (CH)

( * ) Notice: Subject to any disclaimer, the term of this patent is extended or adjusted under 35 U.S.C. 154(b) by 833 days.

(21) Appl. No.: 10/598,777

(22) PCT Filed: Mar. 7, 2005

(86) PCT No.: PCT/EP2005/002362

§ 371 (c)(1),
(2), (4) Date: Sep. 11, 2006

(87) PCT Pub. No.: WO2005/095397

PCT Pub. Date: Oct. 13, 2005

(65) Prior Publication Data

US 2007/0191416 A1   Aug. 16, 2007

(30) Foreign Application Priority Data

Mar. 11, 2004 (WO) ................ PCT/EP2004/002493

(51) Int. Cl.
*A61K 31/4435* (2006.01)
*C07D 457/14* (2006.01)

(52) U.S. Cl. ........................ 546/80; 514/290
(58) Field of Classification Search .................. 514/290; 546/80
See application file for complete search history.

(56) References Cited

U.S. PATENT DOCUMENTS

| 4,808,608 A | 2/1989 | Guindon |
| 5,817,756 A | 10/1998 | Kyle et al. |
| 2004/0162323 A1 | 8/2004 | Krauss |

FOREIGN PATENT DOCUMENTS

| EP | 1170594 | 1/2002 |
| EP | 1413306 | 4/2004 |
| EP | 1435356 | 7/2004 |
| EP | 1 505 061 A1 | 2/2005 |
| GB | 2388540 A | 11/2003 |
| JP | 09216882 A | 8/1997 |
| WO | WO-95/07294 A1 | 3/1995 |
| WO | WO 97/00853 | 1/1997 |
| WO | WO 98/25915 | 6/1998 |
| WO | WO 98/25919 | 6/1998 |
| WO | WO 99/62555 | 12/1999 |
| WO | WO 01/14882 | 3/2001 |
| WO | WO 01/78697 | 10/2001 |
| WO | WO 01/79169 | 10/2001 |
| WO | WO 01/94309 | 12/2001 |
| WO | WO 02/32892 | 4/2002 |
| WO | WO 02/36583 | 5/2002 |
| WO | WO 02/072820 | 9/2002 |
| WO | WO 02/094830 | 11/2002 |
| WO | WO 03/008964 | 1/2003 |
| WO | WO 03/008978 | 1/2003 |
| WO | WO 03/062200 | 7/2003 |
| WO | WO 03/066046 | 8/2003 |
| WO | WO 03/066047 | 8/2003 |
| WO | WO 03/097042 | 11/2003 |
| WO | WO 03/101961 | 12/2003 |
| WO | WO 03/101981 | 12/2003 |
| WO | WO-03/101981 A | 12/2003 |
| WO | WO 2004/007451 | 1/2004 |
| WO | WO 2004/032848 | 4/2004 |
| WO | WO 2004/035543 | 4/2004 |
| WO | WO 2004/039807 | 5/2004 |
| WO | WO 2004/058164 | 7/2004 |
| WO | WO 2004/074240 | 9/2004 |
| WO | WO 2004/078719 | 9/2004 |
| WO | WO 2004/089884 | 10/2004 |
| WO | WO 2004/089885 | 10/2004 |
| WO | WO 2004/096777 | 11/2004 |
| WO | WO 2004/103970 | 12/2004 |
| WO | WO 2004/106302 | 12/2004 |
| WO | WO 2004/111047 | 12/2004 |
| WO | WO 2005/007094 | 1/2005 |
| WO | WO 2005/018529 | 3/2005 |
| WO | WO 2005/019171 | 3/2005 |
| WO | WO 2005/094816 | 10/2005 |
| WO | WO 2006/021418 | 3/2006 |
| WO | WO 2006/070325 | 7/2006 |
| WO | WO 2008/017989 | 2/2008 |

OTHER PUBLICATIONS

Leonard et al.; "Measurement of α- and β-Chemokines"; Current Protocols in Immunology (2000) 6.12.1-6.12.28, Ed. Coligan et al., John & Wiley & Sons, Inc. 1995.

Sugimoto, H. et al.; "An Orally Bioavailable Small Molecule Antagonist of CRTH2, Ramatroban (BAY u3405), Inhibits Prostaglandin $D_2$-Induced Eosinophil Migration in Vitro"; The Journal of Pharmacology and Experimental Therapeutics, vol. 305, No. 1, 2003, pp. 347-352.

(Continued)

*Primary Examiner*—Rita J Desai
(74) *Attorney, Agent, or Firm*—Hunton & Williams LLP

(57) ABSTRACT

The invention relates to tetrahydropyridoindole derivatives and their use as active ingredients in the preparation of pharmaceutical compositions. The invention also concerns related aspects including processes for the preparation of the compounds, pharmaceutical compositions comprising one or more of those compounds and methods of treatment comprising administration of said compounds.

25 Claims, No Drawings

OTHER PUBLICATIONS

Elwood, W. et al.; "Airway Hyperresponsiveness is Associated with Inflammatory Cell Infiltration in Allergic Brown-Norway Rats"; Int Arch Allergy Immunol 1992, 99, pp. 91-97.

Reminton's Pharmaceutical Sciences, 20th Edition, 2001, Marck Publishing Company, Easton, Pennsylvania.

Larock, R.; "Comprehensive Organic Transformations: A Guide to Functional Group Preparations"; Wiley-VCH Publishers, 1999.

Green, T. et al.; "Protective Groups in Organic Synthesis"; Wiley-Interscience 1999.

Block, M. et al.; "Discovery and Optimization of a Series of Carbazole Ureas as NPY5 Antagonists for the Treatment of Obesity"; Journal of Medical Chemistry, 2002, vol. 45, No. 16, pp. 3509-3523.

Sawyer, N., et al.; "Molecular pharmacology of the human prostaglandin $D_2$ receptor, CRTH2"; British Journal of Pharmacology, 2002, vol. 137, pp. 1163-1172.

Ishizuka, T., "Ramatroban (BAY u 3405): A Novel Dual Antagonist of TXA2 Receptor and crtH2, A Newly Identified Prostaglandin D2 Receptor", Cardiovascular Drug Reviews, vol. 22, No. 2, pp. 71-90 (2004).

Robarge, M., "Isosteric Ramatroban Analogs: Selective and Potent CRTH-2 Antagonists", Bioorganic & Medicinal Chemistry Letters 15, pp. 1749-1753 (2005).

Ulven, T., "Minor Structural Modifications Convert the Dual TP/CRTH2 Antagonist Ramatroban into a Highly Selective and Potent CRTH2 Antagonist", Journal of Medicinal Chemistry, 48(4) pp. 897-900, (2005).

TETRAHYDROPYRIDOINDOLE DERIVATIVES

FIELD OF THE INVENTION

The present invention relates to novel tetrahydropyridoindole derivatives and their use as potent CRTH2 receptor antagonists in the treatment of prostaglandin mediated diseases, to pharmaceutical compositions comprising these derivatives and to processes for their preparation. In particular, such derivatives may be used alone or in pharmaceutical compositions for the treatment of both chronic and acute allergic/immune disorders such as allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, basophil-related diseases, such as basophilic leukemia and basophilic leukocytosis in humans and other mammals.

BACKGROUND OF THE INVENTION

Prostaglandin D2 is a known agonist of the thromboxane A2 (TxA2) receptor, the PGD2 (DP) receptor and the recently identified G-protein-coupled "chemoattractant receptor-homologous molecule expressed on Th2 cells" (CRTH2).

The response to allergen exposure in a previously sensitized host results in a cascade effect involving numerous cell types and release of a number of cytokines, chemokines, and multiple mediators. Among these critical initiators are the cytokines interleukin (IL)-4, IL-13, and IL-5, which play critical roles in Th2 cell differentiation, immunoglobulin (Ig)E synthesis, mast cell growth and differentiation, upregulation of CD23 expression, and the differentiation, recruitment, and activation of eosinophils. The stimulated release of the array of mediators, causes end-organ damage, including constriction and hyperresponsiveness, vascular permeability, edema, mucous secretion, and further inflammation.

Because of the number of responses targeted, corticosteroids have proven to be the most effective therapy. Rather than antagonizing these specific responses in a directed way, another approach is to alter the immune response, that is, to change the nature of the immunological response to allergen. CRTH2 is preferentially expressed on Th2 cells and is a chemoattractant receptor for PGD2 that mediates PGD2-dependent migration of blood Th2 cells. Chemoattractants are responsible for the recruitment of both Th2 cells and other effector cells of allergic inflammation, which can provide the conceptual basis for the development of new therapeutic strategies in allergic conditions.

So far, few compounds having CRTH2 antagonistic activity have been reported in the patent literature. Bayer AG claims the use of Ramatroban ((3R)-3-(4-fluorobenzene-sulfonamido)-1,2,3,4-tetrahydrocarbazole-9-propionic acid) for the prophylaxis and treatment of allergic diseases, such as asthma, allergic rhinitis or allergic conjuvatitis (GB 2388540). Further, (2-tert.-butoxycarbonyl-1,2,3,4-tetrahydro-pyrido[4,3-b]indol-5-yl)-acetic acid and (2-ethoxycarbonyl-1,2,3,4-tetrahydro-pyrido[4,3-b]indol-5-yl)-acetic acid are disclosed by Kyle F. et al in two patent applications (U.S. Pat. No. 5,817,756 and WO 9507294, respectively).

Furthermore, oral bioavailability of the Ramatroban and its ability to inhibit prostaglandin D2-induced eosinophil migration in vitro has been reported (*Journal of Pharmacology and Experimental Therapeutics*, 305(1), p. 347-352 (2003)).

DESCRIPTION OF THE INVENTION

It has now been found that compounds of the general Formulae (I) and (II) of the present invention are CRTH2 receptor antagonists. These compounds are useful for the treatment of both chronic and acute allergic/immune disorders such as allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and siniusitis, basophil-related diseases, such as basophilic leukemia and basophilic leukocytosis.

The following paragraphs provide definitions of the various chemical moieties that make up the compounds according to the invention and are intended to apply uniformly throughout the specification and claims unless an otherwise expressly set out definition provides a broader definition.

The term "$C_1$-$C_5$-alkyl", alone or in combination with other groups, means a straight-chain or branched-chain alkyl group with 1-5 carbon atoms as for example methyl, ethyl, propyl, isopropyl, butyl, sec.-butyl, tert.-butyl, isobutyl and the isomeric pentyls. Preferred are groups with 1 to 3 carbon atoms. This $C_1$-$C_5$-alkyl group may optionally be substituted by one to three substituents independently selected from cyano, halogen, hydroxy, cycloalkyl, aryl, $C_2$-$C_5$-alkenyl, $C_1$-$C_5$-alkoxy, $C_2$-$C_5$-alkenyloxy, trifluoromethyl, trifluoromethoxy, amino and carboxy. If $C_1$-$C_5$-alkyl is substituted, it preferably represents trifluoromethyl.

The term "$C_0$-$C_5$-alkyl-carbonyl", alone or in combination with other groups, means an R—CO— group, wherein R" is hydrogen or a $C_1$-$C_5$-alkyl group as defined above; examples are formyl, acetyl, propionyl, butyryl, isobutyryl and the like.

The term "$C_2$-$C_5$-alkenyl-carbonyl", alone or in combination with other groups, means an R'—CO— group, wherein R' is a straight-chain or branched-chain alkenyl group with 2 to 5 carbon atoms; examples are acryl, methacryl, crotonoyl and dimethylacryl.

The term "$C_1$-$C_5$-alkyl-carbamoyl", alone or in combination with other groups, means an R"—NH—CO— group wherein R" is a $C_1$-$C_5$-alkyl group as defined above; examples are methylcarbamoyl, ethylcarbamoyl, propylcarbamoyl, isopropylcarbamoyl, butylcarbamoyl, tert.-butylcarbamoyl and the like.

The term "$C_1$-$C_5$-alkoxy", alone or in combination with other groups, means a group of the Formula R"—O— in which R" is a $C_1$-$C_5$-alkyl group as defined above; examples are methoxy, ethoxy, n-propoxy, isopropoxy, n-butoxy, isobutoxy, sec-butoxy and tert.-butoxy, preferably methoxy and ethoxy.

The term "aryl", alone or in combination with other groups, means an aromatic carbocyclic group from 6 to 14 carbon atoms having a single ring or multiple condensed rings wherein said ring(s) is/are optionally substituted by one or more substituents independently selected from the group consisting of oxo, cyano, halogen, hydroxy, $C_1$-$C_5$-alkyl, $C_2$-$C_5$-alkenyl, $C_1$-$C_5$-alkoxy, $C_2$-$C_5$-alkenyloxy, cycloalkyl, aryl, heteroaryl, trifluoromethyl, trifluoromethoxy, amino and carboxy. Preferred aryl include phenyl or naphthyl which optionally carry one or more substituents, preferably one or two substituents, each independently selected from cyano, halogen, hydroxy, $C_1$-$C_5$-alkyl, $C_2$-$C_5$-alkenyl, $C_1$-$C_5$-alkoxy, $C_2$-$C_5$-alkenyloxy, cycloalkyl, aryl, heteroaryl, trifluoromethyl, trifluoromethoxy, amino and carboxy.

The term "aryl-$C_1$-$C_5$-alkyl", alone or in combination with other groups, means a $C_1$-$C_5$-alkyl group having an aryl substituent in which the aryl group is as defined above.

The term "aryl-carbonyl", alone or in combination with other groups, means a group of the Formula Ar—CO— in which Ar is an aryl group as defined above; examples are phenyl-carbonyl and naphthyl-carbonyl.

The term "aryl-$C_1$-$C_5$-alkyl-carbonyl", alone or in combination with other groups, means a $C_1$-$C_5$-alkyl-carbonyl group having an aryl substituent in which the aryl group is as defined above.

The term "aryl-$C_1$-$C_5$-alkoxy-carbonyl", alone or in combination with other groups, means a $C_1$-$C_5$-alkoxy-carbonyl group having an aryl substituent in which the aryl group is as defined above.

The term "aryl-carbamoyl", alone or in combination with other groups, means a group of the Formula Ar—NH—CO— in which Ar is an aryl group as defined above.

The term "aryl-thiocarbamoyl", alone or in combination with other groups, means a group of the Formula Ar—NH—C(=S)— in which Ar is an aryl group as defined above.

The term "aryl-$C_1$-$C_5$-alkyl-carbamoyl", alone or in combination with other groups, means a group of the Formula Ar—$C_1$-$C_5$-alkyl-NH—CO— in which Ar is an aryl group as defined above.

The term "aryl-$C_1$-$C_5$-alkyl-thiocarbamoyl", alone or in combination with other groups, means a group of the Formula Ar—$C_1$-$C_5$-alkyl-NH—C(=S)— in which Ar is an aryl group as defined above.

The term "cycloalkyl", alone or in combination with other groups, means a saturated cyclic hydrocarbon moiety containing 3-15, preferably 3-6, carbon atoms, optionally substituted by one or more groups, each individually and independently selected from $C_2$-$C_5$-alkenyl, $C_1$-$C_5$-alkoxy, $C_1$-$C_5$-alkoxy-$C_1$-$C_5$-alkyl, $C_1$-$C_5$-alkoxy-carbonyl, $C_1$-$C_5$-alkoxy-carbonyl-$C_1$-$C_5$-alkyl, $C_1$-$C_5$-alkyl, $C_0$-$C_5$-alkyl-carbonyl, $C_0$-$C_5$-alkyl-carbonyl-$C_1$-$C_5$-alkyl, $C_0$-$C_5$-alkyl-carbonyloxy, $C_1$-$C_5$-alkylendioxy, $C_1$-$C_5$-alkylsulfinyl, $C_1$-$C_5$-alkylsulfinyl-$C_1$-$C_5$-alkyl, $C_1$-$C_5$-alkylsulfonyl, $C_1$-$C_5$-alkylsulfonyl-$C_1$-$C_5$-alkyl, $C_1$-$C_5$-alkylthio, $C_1$-$C_5$alkylthio-$C_1$-$C_5$-alkyl, $C_2$-$C_5$-alkynyl, amino, amino-$C_1$-$C_5$-alkyl, aminocarbonyl, aminocarbonyl-$C_1$-$C_5$-alkyl, aryl, aryl-$C_2$-$C_5$-alkenyl, aryl-$C_1$-$C_5$-alkoxy, aryl-$C_1$-$C_5$-alkyl, aryloxy, aryloxycarbonyl, aryloxycarbonyl-$C_1$-$C_5$-alkyl, arylsulfinyl, arylsulfinyl-$C_1$-$C_5$-alkyl, arylsulfonyl, arylsulfonyl-$C_1$-$C_5$-alkyl, arylthio, arylthio-$C_1$-$C_5$-alkyl, carboxy, carboxy-$C_1$-$C_5$-alkyl, cyano, cyano-$C_1$-$C_5$-alkyl, formyl, formyl-$C_1$-$C_5$-alkyl, halogen, haloalkoxy, halo-$C_1$-$C_5$-alkyl, hydroxy, hydroxyl-$C_1$-$C_5$-alkyl, mercapto, and nitro. Preferably, cycloalkyl is unsubstituted. Representative examples of cycloalkyl include, but are not limited to, cyclopropyl, cyclobutyl, cyclopentyl, cyclohexyl, cycloheptyl and cyclooctyl, preferably cyclopropyl, cyclopentyl and cyclohexyl. In polycyclic cycloalkyl groups one of the distal rings may be aromatic, e.g., 1-indanyl, 2-indanyl, tetrahydronaphthalene, and the like.

The term "cycloalkyl-carbonyl", alone or in combination with other groups, means a carbonyl group having a cycloalkyl substituent in which the cycloalkyl group is as defined above.

The term "cycloalkyl-$C_1$-$C_5$-alkyl-carbonyl", alone or in combination with other groups, means a $C_1$-$C_5$-alkyl-carbonyl group having a cycloalkyl substituent in which the cycloalkyl group is as defined above.

The term "cycloalkyl-$C_1$-$C_5$-alkoxy-carbonyl", alone or in combination with other groups, means a $C_1$-$C_5$-alkoxy-carbonyl group having a cycloalkyl substituent in which the cycloalkyl group is as defined above.

The term "cycloalkyl-carbamoyl", alone or in combination with other groups, means a group of the Formula cycloalkyl-NH—C(=S)— wherein the cycloalkyl group is as defined above.

The term "heteroaryl" means a monocyclic heteroaromatic, or a bicyclic or (less preferred) a tricyclic fused-ring heteroaromatic group having preferably 5 to 14, especially 5 to 10 ring members of which 1 to 3, especially 1 or 2, are heteroatoms selected from the group consisting of oxygen, nitrogen and sulphur, while the remaining ring members are carbon atoms. Heteroaryl is optionally substituted by one or more substituents, preferably one or two substituents, each independently selected from cyano, halogen, hydroxy, $C_1$-$C_5$-alkyl, $C_2$-$C_5$-alkenyl, $C_1$-$C_5$-alkoxy, $C_2$-$C_5$-alkenyloxy, cycloalkyl, aryl, heteroaryl, trifluoromethyl, trifluoromethoxy, amino and carboxy. Particular examples of heteroaromatic groups include pyridyl, pyrazinyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, purinyl, pteridinyl, carbazolyl, xanthenyl or benzoquinolyl. Preferred heteroaryl groups include thienyl, pyridyl or furyl, wherein said groups optionally carry one or more substituents, preferably one or two substituents, each independently selected from cyano, halogen, hydroxy, $C_1$-$C_5$-alkyl, $C_2$-$C_5$-alkenyl, $C_1$-$C_5$alkoxy, $C_2$-$C_5$-alkenyloxy, cycloalkyl, aryl, heteroaryl, trifluoromethyl, trifluoromethoxy, amino and carboxy.

The term "heteroaryl-$C_1$-$C_5$-alkyl", alone or in combination with other groups, means a $C_1$-$C_5$-alkyl group having a heteroaryl substituent in which the heteroaryl group is as defined above.

The term "heteroaryl-carbonyl", alone or in combination with other groups, means a group of the Formula Het-CO— in which Het is a heteroaryl group as defined above.

The term "heteroaryl-$C_1$-$C_5$-alkyl-carbonyl", alone or in combination with other groups, means a group of the Formula Het-$C_1$-$C_5$-alkyl-CO— in which Het is a heteroaryl group as defined above.

The term "heteroaryl-$C_1$-$C_5$-alkoxy-carbonyl", alone or in combination with other groups, means a group of the Formula Het-$C_1$-$C_5$-alkoxy-CO— in which Het is a heteroaryl group as defined above.

The term "halogen" means fluorine, chlorine, bromine or iodine, preferably fluorine, chlorine and bromine.

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or polyacid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used farther as intermediates, it is also possible to use pharmaceutically unacceptable salts, e.g. the picrates. Only pharmaceutically acceptable, non-toxic salts may be used for therapeutic purposes, however, and those salts are therefore preferred.

The expression "pharmaceutically acceptable salts" encompasses either salts with inorganic acids or organic acids like hydrochloric or hydrobromic acid, sulfuric acid, phosphoric acid, citric acid, formic acid, acetic acid, maleic acid, tartaric acid, benzoic acid, methanesulfonic acid, p-toluenesulfonic acid, and the like that are non-toxic to living organisms. In case the compound of general Formula (I) is acidic in nature the expression encompasses salts with an inorganic base like an alkali or earth alkali base, e.g. sodium hydroxide, potassium hydroxide, calcium hydroxide, and the like which are also non-toxic to living organisms.

A first aspect of the present invention relates to novel tetrahydropyridoindole derivatives of the general Formula (I):

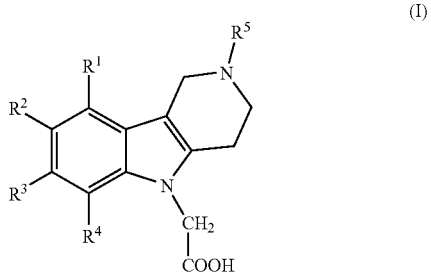

wherein $R^1$, $R^2$, $R^3$ and $R^4$ independently represent hydrogen, $C_1$-$C_5$-alkyl, $C_1$-$C_5$-alkoxy, halogen, nitro, cyano or formyl; and $R^5$ represents $C_0$-$C_5$-alkyl-carbonyl, $C_2$-$C_5$-alkenyl-carbonyl, $C_1$-$C_5$-alkoxy-carbonyl, $C_1$-$C_5$-alkyl, $C_1$-$C_5$-alkyl-carbamoyl, aryl-$C_1$-$C_5$-alkyl, aryl-carbonyl, aryl-$C_1$-$C_5$-alkyl-carbonyl, aryl-$C_1$-$C_5$-alkoxy-carbonyl, aryl-carbamoyl, aryl-thiocarbamoyl, aryl-$C_1$-$C_5$alkyl-carbamoyl, aryl-$C_1$-$C_5$-alkyl-thiocarbamoyl, cycloalkyl-carbonyl, cycloalkyl-$C_1$-$C_5$-alkyl-carbonyl, cycloalkyl-$C_1$-$C_5$-alkoxy-carbonyl, cycloalkyl-carbamoyl, heteroaryl-$C_1$-$C_5$-alkyl, heteroaryl-carbonyl, heteroaryl-$C_1$-$C_5$-alkyl-carbonyl or heteroaryl-$C_1$-$C_5$-alkoxy-carbonyl;

with the proviso that when $R^1$, $R^2$, $R^3$ and $R^4$ represent hydrogen, $R^5$ is not an ethoxy-carbonyl group or a tert.-butoxycarbonyl group;

and optically pure enantiomers, mixtures of enantiomers, racemates, optically pure diastereoisomers, mixtures of diastereoisomers, diastereoisomeric racemates, mixtures of diastereoisomeric racemates, meso forms, and salts thereof.

The present invention also relates to tetrahydropyridoindole derivatives of the general Formula (I), wherein $R^1$, $R^2$, $R^3$ and $R^4$ independently represent hydrogen, $C_1$-$C_5$-alkyl, $C_1$-$C_5$-alkoxy, halogen, nitro, cyano or formyl; and $R^5$ represents $C_0$-$C_5$-alkyl-carbonyl, $C_2$-$C_5$-alkenyl-carbonyl, $C_1$-$C_5$-alkoxy-carbonyl, $C_1$-$C_5$alkyl, $C_1$-$C_5$-alkyl-carbamoyl, aryl-$C_1$-$C_5$-alkyl, aryl-carbonyl, aryl-$C_1$-$C_5$-alkyl-carbonyl, aryl-$C_1$-$C_5$-alkoxy-carbonyl, aryl-carbamoyl, cycloalkyl-carbonyl, cycloalkyl-$C_1$-$C_5$-alkyl-carbonyl, cycloalkyl-$C_1$-$C_5$-alkoxy-carbonyl, heteroaryl-$C_1$-$C_5$-alkyl, heteroaryl-carbonyl, heteroaryl-$C_1$-$C_5$-alkyl-carbonyl or heteroaryl-$C_1$-$C_5$-alkoxy-carbonyl;

with the proviso that when $R^1$, $R^2$, $R^3$ and $R^4$ represent hydrogen, $R^5$ is not an ethoxy-carbonyl group or a tert.-butoxycarbonyl group.

In a preferred embodiment, the present invention relates to tetrahydropyridoindole derivatives of the general Formula (I), wherein $R^1$, $R^2$, $R^3$ and $R^4$ independently represent hydrogen, $C_1$-$C_5$-alkyl, $C_1$-$C_5$-alkoxy or halogen; and $R^5$ represents $C_0$-$C_5$-alkyl-carbonyl, $C_2$-$C_5$-alkenyl-carbonyl, $C_1$-$C_5$-alkoxy-carbonyl, $C_1$-$C_5$alkyl-carbamoyl, aryl-$C_1$-$C_5$-alkyl, aryl-carbonyl, aryl-$C_1$-$C_5$-alkyl-carbonyl, aryl-$C_1$-$C_5$-alkoxy-carbonyl, aryl-carbamoyl, aryl-thiocarbamoyl, aryl-$C_1$-$C_5$-alkyl-carbamoyl, aryl-$C_1$-$C_5$-alkyl-thiocarbamoyl, cycloalkyl-carbonyl, cycloalkyl-$C_1$-$C_5$-alkyl-carbonyl, cycloalkyl-carbamoyl or heteroaryl-carbonyl;

with the proviso that when $R^1$, $R^2$, $R^3$ and $R^4$ represent hydrogen, $R^5$ is not an ethoxy-carbonyl group or a tert.-butoxycarbonyl group.

Any reference hereinabove or hereinbelow to a compound of general Formula (I) or (II) is to be understood as referring also to optically pure enantiomers, mixtures of enantiomers, racemates, optically pure diastereoisomers, mixtures of diastereoisomers, diastereoisomeric racemates, mixtures of diastereoisomeric racemates, meso forms and salts [only pharmaceutically acceptable ones in case of a compound of general Formula (II)] of such compounds, as appropriate and expedient.

Preferred tetrahydropyridoindole derivatives of general Formula (I) are those wherein $R^1$, $R^2$, $R^3$ and $R^4$ represent hydrogen.

In a preferred embodiment, $R^1$, $R^2$, $R^3$ and $R^4$ independently represent $C_1$-$C_5$-alkyl, $C_1$-$C_3$alkoxy, halogen, nitro, cyano or formyl, especially $C_1$-$C_5$-alkyl, $C_1$-$C_3$-alkoxy or halogen.

In another preferred embodiment one or two substituents selected from $R^1$, $R^2$, $R^3$ and $R^4$ independently represent methyl, trifluoromethyl, methoxy, fluoro, chloro or bromo.

In a very preferred embodiment $R^2$ is selected from $C_1$-$C_5$-alkyl, $C_1$-$C_5$-alkoxy, halogen and trifluoromethyl, especially from $C_1$-$C_5$-alkyl, halogen and trifluoromethyl; $R^3$ is hydrogen or halogen, especially hydrogen; and $R^1$ and $R^4$ are both hydrogen.

In a most especially preferred embodiment $R^2$ is selected from methyl, fluoro, chloro, bromo and trifluoromethyl; $R^3$ is hydrogen or chloro, especially hydrogen; and $R^1$ and $R^4$ are both hydrogen.

In a particularly preferred embodiment, $R^5$ is selected from the group consisting of 2-cyclohexyl-2-phenyl-acetyl; 2-naphthalen-1-yl-acetyl; 2-naphthalen-2-yl-acetyl; 3-cyclopentyl-propionyl; 3-phenyl-propionyl; acetyl; diphenylacetyl; hexanoyl; (E)-but-2-enoyl; 9H-fluoren-9-yl-methoxycarbonyl; benzyloxycarbonyl; butoxycarbonyl; 3-phenyl-propyl; phenethyl; phenylacetyl; ethylcarbamoyl;

2-bromo-3-methyl-benzoyl; 2-bromo-5-methyl-benzoyl; 2-methoxy-benzoyl; 3,4,5-trimethoxy-benzoyl; 3,5-bis-trifluoromethyl-benzoyl; 3,5-dimethoxy-benzoyl; 3-chlorobenzoyl; 4-bromo-benzoyl; 4-chloro-benzoyl; 4-methoxybenzoyl; 4-tert.-butyl-benzoyl; 4-trifluoromethoxy-benzoyl, 4-trifluoromethyl-benzoyl; benzoyl; phenylcarbamoyl; 4'-ethyl-biphenyl-4-carbonyl; biphenyl-2-carbonyl; biphenyl-4-carbonyl; 2-methoxy-naphthalene-1-carbonyl; 4-methoxy-naphthalene-1-carbonyl; 2-ethoxy-naphthalene-1-carbonyl; naphthalene-1-carbonyl; cyclohexane-carbonyl; cyclopropane-carbonyl; pyridine-3-carbonyl; 2-chloro-6-methyl-pyridine-4-carbonyl; pyridine-4-carbonyl; furan-2-carbonyl; furan-3-carbonyl; 2-methyl-furan-3-carbonyl; 3-methyl-furan-2-carbonyl; 5-bromo-furan-2-carbonyl; pyrazine-2-carbonyl, benzo[b]thiophene-2-carbonyl; 5-chloro-thiophene-2-carbonyl; 3-methyl-thiophene-2-carbonyl; 5-methyl-thiophene-2-carbonyl; thiophene-2-carbonyl and thiophene-3-carbonyl.

Very preferably $R^5$ represents phenyl-carbonyl or naphthyl-carbonyl (especially naphthalene-1-carbonyl), wherein the phenyl or naphthyl moiety is optionally substituted by one or more, especially by one or two, substituents selected from $C_1$-$C_5$-alkyl, $C_1$-$C_5$-alkoxy and halogen. If $R^5$ represents substituted phenyl-carbonyl, the substituents are preferably selected from $C_1$-$C_5$-alkyl, such as especially methyl, and halogen, such as especially fluoro, chloro and bromo. If $R^5$ represents substituted naphthyl-carbonyl, the substituents are preferably selected from $C_1$-$C_5$-alkoxy, such as especially methoxy and ethoxy, and halogen, such as especially fluoro.

A group of preferred compounds are those wherein $R^1$, $R^2$, $R^3$ and $R^4$ represent hydrogen, $R^5$ represents a $C_1$-$C_5$-alkoxy-carbonyl group, an aryl-$C_1$-$C_5$-alkyl-carbonyl group, an arylcarbonyl group or a heteroaryl-carbonyl group, especially an aryl-carbonyl group, very preferably naphthalene-1-carbonyl.

Another group of preferred compounds are those wherein $R^1$, $R^2$, $R^3$ and $R^4$ represent hydrogen and $R^5$ represents a $C_1$-$C_5$-alkoxy-carbonyl group, a phenyl $C_1$-$C_5$-alkyl-carbonyl group, a naphthalene-1-carbonyl group or a thiophene-2-carbonyl group.

In a preferred embodiment the present invention relates to tetrahydropyridoindole derivatives of the general Formula (I), wherein $R^1$, $R^2$, $R^3$ and $R^4$ independently represent hydrogen, $C_1$-$C_5$-alkyl, $C_1$-$C_3$-alkoxy or halogen; and $R^5$ represents $C_0$-$C_5$-alkyl-carbonyl; $C_1$-$C_5$-alkyl-carbamoyl; $C_1$-$C_5$-alkoxy-carbonyl; $C_2$-$C_5$alkenyl-carbonyl; $C_3$-$C_6$-cycloalkyl-carbonyl; $C_3$-$C_6$-cycloalkyl-$C_1$-$C_3$-alkyl-carbonyl; $C_3$-$C_6$-cycloalkyl-carbamoyl; $C_3$-$C_6$-cycloalkyl-thiocarbamoyl; phenyl-$C_1$-$C_3$-alkyl; phenyl-carbonyl or phenyl-$C_1$-$C_3$-alkyl-carbonyl wherein the phenyl moiety of these two groups may be mono-, di-, tri- or tetra-substituted by substituents independently selected from $C_1$-$C_4$-alkyl, $C_1$-$C_3$-alkoxy, halogen, trifluoromethyl and trifluoromethoxy, mono-substituted by $C_3$-$C_6$-cycloalkyl, or mono-substituted by a phenyl group which in turn may be substituted by a $C_1$-$C_3$-alkyl or $C_1$-$C_3$-alkoxy group; phenyl-$C_1$-$C_3$-alkoxy-carbonyl; phenyl-carbamoyl or phenyl-thiocarbamoyl wherein these two groups are optionally independently mono- or poly-substituted by $C_1$-$C_5$-alkyl and/or halogen; phenyl-$C_1$-$C_3$-alkyl-carbamoyl; phenyl-$C_1$-$C_3$-alkyl-thiocarbamoyl; biphenyl-carbamoyl; naphthyl-carbonyl, naphthyl-$C_1$-$C_3$-alkyl-carbonyl or naphthyl-carbamoyl wherein the naphthyl moieties of these three groups are optionally mono- or poly-substituted by substituents independently selected from $C_1$-$C_3$-alkyl, $C_1$-$C_3$-alkoxy and halogen; fluorenyl-carbonyl, optionally substituted by oxo; fluorenyl-$C_1$-$C_3$-alkoxy-carbonyl; or five- to nine-membered heteroaryl-carbonyl groups containing one to three, preferably 1 or 2, heteroatoms independently selected from oxygen, nitrogen and sulfur wherein said groups may be substituted by one or two groups independently selected from $C_1$-$C_3$-alkyl, $C_1$-$C_3$-alkoxy, halogen and trifluoromethyl;

with the proviso that when $R^1$, $R^2$, $R^3$ and $R^4$ represent hydrogen, $R^5$ is not an ethoxy-carbonyl group or a tert.-butoxycarbonyl group.

The present invention also relates to tetrahydropyridoindole derivatives of the general Formula (I), wherein $R^1$, $R^2$, $R^3$ and $R^4$ independently represent hydrogen, $C_1$-$C_5$-alkyl, $C_1$-$C_3$-alkoxy or halogen; and $R^5$ represents $C_0$-$C_5$-alkyl-carbonyl; $C_1$-$C_5$-alkoxy-carbonyl; $C_2$-$C_5$-alkenyl-carbonyl; $C_3$-$C_6$-cycloalkyl-carbonyl; $C_3$-$C_6$-cycloalkyl-$C_1$-$C_3$-alkyl-carbonyl; $C_3$-$C_6$-cycloalkyl-$C_1$-$C_3$-alkoxy-carbonyl; phenyl-carbonyl or phenyl-$C_1$-$C_3$-alkyl-carbonyl wherein the phenyl moiety of said groups may be independently mono-, di- or tri-substituted by $C_1$-$C_4$-alkyl, $C_1$-$C_3$-alkoxy, halogen, trifluoromethyl or trifluoromethoxy, or mono-substituted by a phenyl group which in turn may be substituted by a $C_1$-$C_3$-alkyl or $C_1$-$C_3$-alkoxy group; naphthyl-carbonyl; fluorenyl-$C_1$-$C_3$-alkoxy-carbonyl; or five- or six-membered heteroaryl-carbonyl groups containing one to three heteroatoms independently selected from oxygen, nitrogen and sulfur wherein said groups may be substituted by one or two groups independently selected from $C_1$-$C_3$-alkyl, $C_1$-$C_3$-alkoxy, halogen and trifluoromethyl; with the proviso that when $R^1$, $R^2$, $R^3$ and $R^4$ represent hydrogen, $R^5$ is not an ethoxy-carbonyl group or a tert.-butoxycarbonyl group.

Examples of preferred compounds of general Formula (I) are selected from the group consisting of:

(2-benzyloxycarbonyl-1,2,3,4-tetrahydro-pyrido[4,3-b]indol-5-yl)-acetic acid;

(2-butoxycarbonyl-1,2,3,4-tetrahydro-pyrido[4,3-b]indol-5-yl)-acetic acid;

(2-9H-fluoren-9-ylmethoxycarbonyl-1,2,3,4-tetrahydro-pyrido[4,3-b]indol-5-yl)-acetic acid;

(2-acetyl-1,2,3,4-tetrahydro-pyrido[4,3-b]indol-5-yl)-acetic acid;

(2-phenylacetyl-1,2,3,4-tetrahydro-pyrido[4,3-b]indol-5-yl)-acetic acid;

(2-benzoyl-1,2,3,4-tetrahydro-pyrido[4,3-b]indol-5-yl)-acetic acid;

[2-(3,4,5-trimethoxy-benzoyl)-1,2,3,4-tetrahydro-pyrido[4,3-b]indol-5-yl]-acetic acid;

(2-cyclohexanecarbonyl-1,2,3,4-tetrahydro-pyrido[4,3-b]indol-5-yl)-acetic acid;

[2-(4-methoxy-benzoyl)-1,2,3,4-tetrahydro-pyrido[4,3-b]indol-5-yl]-acetic acid;

[2-(thiophene-2-carbonyl)-1,2,3,4-tetrahydro-pyrido[4,3-b]indol-5-yl]-acetic acid;

[2-(furan-2-carbonyl)-1,2,3,4-tetrahydro-pyrido[4,3-b]indol-5-yl]-acetic acid;

(2-cyclopropanecarbonyl-1,2,3,4-tetrahydro-pyrido[4,3-b]indol-5-yl)-acetic acid;

[2-(naphthalene-1-carbonyl)-1,2,3,4-tetrahydro-pyrido[4,3-b]indol-5-yl]-acetic acid;

[2-(2-methoxy-benzoyl)-1,2,3,4-tetrahydro-pyrido[4,3-b]indol-5-yl]-acetic acid;

[2-(4-trifluoromethyl-benzoyl)-1,2,3,4-tetrahydro-pyrido[4,3-b]indol-5-yl]-acetic acid;

[2-(3,5-bis-trifluoromethyl-benzoyl)-1,2,3,4-tetrahydro-pyrido[4,3-b]indol-5-yl]-acetic acid;
[2-(3-cyclopentyl-propionyl)-1,2,3,4-tetrahydro-pyrido[4,3-b]indol-5-yl]-acetic acid;
[2-(3-phenyl-propionyl)-1,2,3,4-tetrahydro-pyrido[4,3-b]indol-5-yl]-acetic acid;
[2-(biphenyl-4-carbonyl)-1,2,3,4-tetrahydro-pyrido[4,3-b]indol-5-yl]-acetic acid;
[2-(4-tert.-butyl-benzoyl)-1,2,3,4-tetrahydro-pyrido[4,3-b]indol-5-yl]-acetic acid;
[2-(4-trifluoromethoxy-benzoyl)-1,2,3,4-tetrahydro-pyrido[4,3-b]indol-5-yl]-acetic acid;
[2-((E)-but-2-enoyl)-1,2,3,4-tetrahydro-pyrido[4,3-b]indol-5-yl]-acetic acid;
[2-(4-chloro-benzoyl)-1,2,3,4-tetrahydro-pyrido[4,3-b]indol-5-yl]-acetic acid;
[2-(3,5-dimethoxy-benzoyl)-1,2,3,4-tetrahydro-pyrido[4,3-b]indol-5-yl]-acetic acid;
(2-diphenylacetyl-1,2,3,4-tetrahydro-pyrido[4,3-b]indol-5-yl)-acetic acid;
(2-hexanoyl-1,2,3,4-tetrahydro-pyrido[4,3-b]indol-5-yl)-acetic acid;
[2-(3-chloro-benzoyl)-1,2,3,4-tetrahydro-pyrido[4,3-b]indol-5-yl]-acetic acid;
[2-(4-bromo-benzoyl)-1,2,3,4-tetrahydro-pyrido[4,3-b]indol-5-yl]-acetic acid;
[2-(pyridine-3-carbonyl)-1,2,3,4-tetrahydro-pyrido[4,3-b]indol-5-yl]-acetic acid;
(2-benzoyl-8-methoxy-1,2,3,4-tetrahydro-pyrido[4,3-b]indol-5-yl)-acetic acid;
(2-benzoyl-7-methyl-1,2,3,4-tetrahydro-pyrido[4,3-b]indol-5-yl)-acetic acid;
(2-benzoyl-8-bromo-1,2,3,4-tetrahydro-pyrido[4,3-b]indol-5-yl)-acetic acid;
(2-benzoyl-8-methyl-1,2,3,4-tetrahydro-pyrido[4,3-b]indol-5-yl)-acetic acid;
(2-benzoyl-6-methyl-1,2,3,4-tetrahydro-pyrido[4,3-b]indol-5-yl)-acetic acid;
[2-(pyrazine-2-carbonyl)-1,2,3,4-tetrahydro-pyrido[4,3-b]indol-5-yl]-acetic acid;
[2-(2-bromo-3-methyl-benzoyl)-1,2,3,4-tetrahydro-pyrido[4,3-b]indol-5-yl]-acetic acid;
[2-(4'-ethyl-biphenyl-4-carbonyl)-1,2,3,4-tetrahydro-pyrido[4,3-b]indol-5-yl]-acetic acid;
[2-(2-bromo-5-methyl-benzoyl)-1,2,3,4-tetrahydro-pyrido[4,3-b]indol-5-yl]-acetic acid;
[2-(2-chloro-6-methyl-pyridine-4-carbonyl)-1,2,3,4-tetrahydro-pyrido[4,3-b]indol-5-yl]-acetic acid;
[2-(biphenyl-2-carbonyl)-1,2,3,4-tetrahydro-pyrido[4,3-b]indol-5-yl]-acetic acid;
[2-(5-bromo-furan-2-carbonyl)-1,2,3,4-tetrahydro-pyrido[4,3-b]indol-5-yl]-acetic acid;
[2-(3-methyl-furan-2-carbonyl)-1,2,3,4-tetrahydro-pyrido[4,3-b]indol-5-yl]-acetic acid;
[2-(2-methyl-furan-3-carbonyl)-1,2,3,4-tetrahydro-pyrido[4,3-b]indol-5-yl]-acetic acid;
[2-(benzo[b]thiophene-2-carbonyl)-1,2,3,4-tetrahydro-pyrido[4,3-b]indol-5-yl]-acetic acid;
[2-(5-chloro-thiophene-2-carbonyl)-1,2,3,4-tetrahydro-pyrido[4,3-b]indol-5-yl]-acetic acid;
[2-(furan-3-carbonyl)-1,2,3,4-tetrahydro-pyrido[4,3-b]indol-5-yl]-acetic acid;
[2-(2-naphthalen-2-yl-acetyl)-1,2,3,4-tetrahydro-pyrido[4,3-b]indol-5-yl]-acetic acid;
[2-(thiophene-3-carbonyl)-1,2,3,4-tetrahydro-pyrido[4,3-b]indol-5-yl]-acetic acid;
[2-(2-naphthalen-1-yl-acetyl)-1,2,3,4-tetrahydro-pyrido[4,3-b]indol-5-yl]-acetic acid;
rac. [2-(2-cyclohexyl-2-phenyl-acetyl)-1,2,3,4-tetrahydro-pyrido[4,3-b]indol-5-yl]-acetic acid;
(2-phenylcarbamoyl-1,2,3,4-tetrahydro-pyrido[4,3-b]indol-5-yl)-acetic acid;
(2-ethylcarbamoyl-1,2,3,4-tetrahydro-pyrido[4,3-b]indol-5-yl)-acetic acid;
sodium (2-phenethyl-1,2,3,4-tetrahydro-pyrido[4,3-b]indol-5-yl)-acetate;
sodium [2-(3-phenyl-propyl)-1,2,3,4-tetrahydro-pyrido[4,3-b]indol-5-yl]-acetate;
[2-(2-ethoxy-naphthalene-1-carbonyl)-1,2,3,4-tetrahydro-pyrido[4,3-b]indol-5-yl]-acetic acid;
[2-(3-methyl-thiophene-2-carbonyl)-1,2,3,4-tetrahydro-pyrido[4,3-b]indol-5-yl]-acetic acid;
[2-(5-methyl-thiophene-2-carbonyl)-1,2,3,4-tetrahydro-pyrido[4,3-b]indol-5-yl]-acetic acid; and
[2-(pyridine-4-carbonyl)-1,2,3,4-tetrahydro-pyrido[4,3-b]indol-5-yl]-acetic acid.

Specifically preferred compounds according to general Formula (I) are:
[2-(naphthalene-1-carbonyl)-1,2,3,4-tetrahydro-pyrido[4,3-b]indol-5-yl]-acetic acid;
[2-(3-chloro-benzoyl)-1,2,3,4-tetrahydro-pyrido[4,3-b]indol-5-yl]-acetic acid;
[2-(4'-ethyl-biphenyl-4-carbonyl)-1,2,3,4-tetrahydro-pyrido[4,3-b]indol-5-yl]-acetic acid;
[2-(2-bromo-3-methyl-benzoyl)-1,2,3,4-tetrahydro-pyrido[4,3-b]indol-5-yl]-acetic acid;
(2-benzoyl-8-bromo-1,2,3,4-tetrahydro-pyrido[4,3-b]indol-5-yl)-acetic acid;
(2-benzoyl-1,2,3,4-tetrahydro-pyrido[4,3-b]indol-5-yl)-acetic acid;
[2-(4-bromo-benzoyl)-1,2,3,4-tetrahydro-pyrido[4,3-b]indol-5-yl] acetic acid; and
[2-(furan-2-carbonyl)-1,2,3,4-tetrahydro-pyrido[4,3-b]indol-5-yl] acetic acid.

In a further very preferred embodiment, the invention relates to a compound of general Formula (I) selected from the group consisting of:
5-carboxymethyl-7-chloro-1,3,4,5-tetrahydro-pyrido[4,3-b]indole-2-carboxylic acid tert-butyl ester;
5-carboxymethyl-8-chloro-1,3,4,5-tetrahydro-pyrido[4,3-b]indole-2-carboxylic acid tert-butyl ester;
5-carboxymethyl-6-chloro-1,3,4,5-tetrahydro-pyrido[4,3-b]indole-2-carboxylic acid tert-butyl ester;
5-carboxymethyl-7-methyl-1,3,4,5-tetrahydro-pyrido[4,3-b]indole-2-carboxylic acid tert-butyl ester;
5-carboxymethyl-8-methyl-1,3,4,5-tetrahydro-pyrido[4,3-b]indole-2-carboxylic acid tert-butyl ester;
8-bromo-5-carboxymethyl-1,3,4,5-tetrahydro-pyrido[4,3-b]indole-2-carboxylic acid tert-butyl ester;
5-carboxymethyl-8-fluoro-1,3,4,5-tetrahydro-pyrido[4,3-b]indole-2-carboxylic acid tert-butyl ester;
[7-chloro-2-(3-chloro-benzoyl)-1,2,3,4-tetrahydro-pyrido[4,3-b]indol-5-yl]-acetic acid;
[8-chloro-2-(3-chloro-benzoyl)-1,2,3,4-tetrahydro-pyrido[4,3-b]indol-5-yl]-acetic acid;
[6-chloro-2-(3-chloro-benzoyl)-1,2,3,4-tetrahydro-pyrido[4,3-b]indol-5-yl]-acetic acid;
[2-(3-chloro-benzoyl)-7-methyl-1,2,3,4-tetrahydro-pyrido[4,3-b]indol-5-yl]-acetic acid;
[2-(3-chloro-benzoyl)-8-methyl-1,2,3,4-tetrahydro-pyrido[4,3-b]indol-5-yl]-acetic acid;
[8-bromo-2-(3-chloro-benzoyl)-1,2,3,4-tetrahydro-pyrido[4,3-b]indol-5-yl]-acetic acid;

[2-(3-chloro-benzoyl)-8-fluoro-1,2,3,4-tetrahydro-pyrido[4,3-b]indol-5-yl]-acetic acid;
[8-chloro-2-(thiophene-2-carbonyl)-1,2,3,4-tetrahydro-pyrido[4,3-b]indol-5-yl]-acetic acid;
[6-chloro-2-(thiophene-2-carbonyl)-1,2,3,4-tetrahydro-pyrido[4,3-b]indol-5-yl]-acetic acid;
[8-bromo-2-(thiophene-2-carbonyl)-1,2,3,4-tetrahydro-pyrido[4,3-b]indol-5-yl]-acetic acid;
[8-fluoro-2-(thiophene-2-carbonyl)-1,2,3,4-tetrahydro-pyrido[4,3-b]indol-5-yl]-acetic acid;
[7-chloro-2-(thiophene-2-carbonyl)-1,2,3,4-tetrahydro-pyrido[4,3-b]indol-5-yl]-acetic acid;
[7-methyl-2-(thiophene-2-carbonyl)-1,2,3,4-tetrahydro-pyrido[4,3-b]indol-5-yl]-acetic acid;
[8-methyl-2-(thiophene-2-carbonyl)-1,2,3,4-tetrahydro-pyrido[4,3-b]indol-5-yl]-acetic acid;
[8-fluoro-2-(2-methoxy-naphthalene-1-carbonyl)-1,2,3,4-tetrahydro-pyrido[4,3-b]indol-5-yl]-acetic acid;
[8-fluoro-2-(4-methoxy-naphthalene-1-carbonyl)-1,2,3,4-tetrahydro-pyrido[4,3-b]indol-5-yl]-acetic acid;
[8-chloro-2-(2-methoxy-naphthalene-1-carbonyl)-1,2,3,4-tetrahydro-pyrido[4,3-b]indol-5-yl]-acetic acid;
[8-chloro-2-(4-methoxy-naphthalene-1-carbonyl)-1,2,3,4-tetrahydro-pyrido[4,3-b]indol-5-yl]-acetic acid;
[2-(2-methoxy-naphthalene-1-carbonyl)-8-methyl-1,2,3,4-tetrahydro-pyrido[4,3-b]indol-5-yl]-acetic acid;
[2-(4-methoxy-naphthalene-1-carbonyl)-8-methyl-1,2,3,4-tetrahydro-pyrido[4,3-b]indol-5-yl]-acetic acid;
[2-(2-methoxy-naphthalene-1-carbonyl)-7-methyl-1,2,3,4-tetrahydro-pyrido[4,3-b]indol-5-yl]-acetic acid;
[2-(2-ethoxy-naphthalene-1-carbonyl)-8-methyl-1,2,3,4-tetrahydro-pyrido[4,3-b]indol-5-yl]-acetic acid;
[2-(2-ethoxy-naphthalene-1-carbonyl)-7-methyl-1,2,3,4-tetrahydro-pyrido[4,3-b]indol-5-yl]-acetic acid;
[2-(4-methoxy-naphthalene-1-carbonyl)-7-methyl-1,2,3,4-tetrahydro-pyrido[4,3-b]indol-5-yl]-acetic acid;
[2-(2-fluoro-benzoyl)-1,2,3,4-tetrahydro-pyrido[4,3-b]indol-5-yl]-acetic acid;
[2-(3-fluoro-benzoyl)-1,2,3,4-tetrahydro-pyrido[4,3-b]indol-5-yl]-acetic acid;
[2-(3,5-difluoro-benzoyl)-1,2,3,4-tetrahydro-pyrido[4,3-b]indol-5-yl]-acetic acid;
[2-(3,4,5-trifluoro-benzoyl)-1,2,3,4-tetrahydro-pyrido[4,3-b]indol-5-yl]-acetic acid;
[2-(2,3,4,5-tetrafluoro-benzoyl)-1,2,3,4-tetrahydro-pyrido[4,3-b]indol-5-yl]-acetic acid;
(2-benzoyl-8-fluoro-1,2,3,4-tetrahydro-pyrido[4,3-b]indol-5-yl)-acetic acid;
(2-benzoyl-6-chloro-1,2,3,4-tetrahydro-pyrido[4,3-b]indol-5-yl)-acetic acid;
(2-benzoyl-8-isopropyl-1,2,3,4-tetrahydro-pyrido[4,3-b]indol-5-yl)-acetic acid;
(2-benzoyl-8-chloro-1,2,3,4-tetrahydro-pyrido[4,3-b]indol-5-yl)-acetic acid;
(2-benzoyl-7,8-dichloro-1,2,3,4-tetrahydro-pyrido[4,3-b]indol-5-yl)-acetic acid;
(2-benzoyl-8-trifluoromethyl-1,2,3,4-tetrahydro-pyrido[4,3-b]indol-5-yl)-acetic acid;
(2-benzoyl-8-tert-butyl-1,2,3,4-tetrahydro-pyrido[4,3-b]indol-5-yl)-acetic acid;
(2-benzoyl-7-chloro-8-methyl-1,2,3,4-tetrahydro-pyrido[4,3-b]indol-5-yl)-acetic acid;
5 (2-benzoyl-7,8-dimethyl-1,2,3,4-tetrahydro-pyrido[4,3-b]indol-5-yl)-acetic acid;
(2-benzoyl-7-fluoro-1,2,3,4-tetrahydro-pyrido[4,3-b]indol-5-yl)-acetic acid;
[7-chloro-2-(2-naphthalen-1-yl-acetyl)-1,2,3,4-tetrahydro-pyrido[4,3-b]indol-5-yl]-acetic acid;
[8-chloro-2-(2-naphthalen-1-yl-acetyl)-1,2,3,4-tetrahydro-pyrido[4,3-b]indol-5-yl]-acetic acid;
[7-methyl-2-(2-naphthalen-1-yl-acetyl)-1,2,3,4-tetrahydro-pyrido[4,3-b]indol-5-yl]-acetic acid;
[8-bromo-2-(2-naphthalen-1-yl-acetyl)-1,2,3,4-tetrahydro-pyrido[4,3-b]indol-5-yl]-acetic acid;
[2-(4'-ethyl-biphenyl-4-carbonyl)-7-methyl-1,2,3,4-tetrahydro-pyrido[4,3-b]indol-5-yl]-acetic acid;
[8-bromo-2-(4'-ethyl-biphenyl-4-carbonyl)-1,2,3,4-tetrahydro-pyrido[4,3-b]indol-5-yl]-acetic acid;
[2-(4'-ethyl-biphenyl-4-carbonyl)-8-fluoro-1,2,3,4-tetrahydro-pyrido[4,3-b]indol-5-yl]-acetic acid;
[6-chloro-2-(4'-ethyl-biphenyl-4-carbonyl)-1,2,3,4-tetrahydro-pyrido[4,3-b]indol-5-yl]-acetic acid;
[7-chloro-2-(4'-ethyl-biphenyl-4-carbonyl)-1,2,3,4-tetrahydro-pyrido[4,3-b]indol-5-yl]-acetic acid;
[8-chloro-2-(4'-ethyl-biphenyl-4-carbonyl)-1,2,3,4-tetrahydro-pyrido[4,3-b]indol-5-yl]-acetic acid;
[2-(4'-ethyl-biphenyl-4-carbonyl)-8-methyl-1,2,3,4-tetrahydro-pyrido[4,3-b]indol-5-yl]-acetic acid;
[8-methyl-2-(2-naphthalen-1-yl-acetyl)-1,2,3,4-tetrahydro-pyrido[4,3-b]indol-5-yl]-acetic acid;
[6-chloro-2-(2-naphthalen-1-yl-acetyl)-1,2,3,4-tetrahydro-pyrido[4,3-b]indol-5-yl]-acetic acid;
[8-chloro-2-(naphthalene-1-carbonyl)-1,2,3,4-tetrahydro-pyrido[4,3-b]indol-5-yl]-acetic acid;
[6-chloro-2-(naphthalene-1-carbonyl)-1,2,3,4-tetrahydro-pyrido[4,3-b]indol-5-yl]-acetic acid;
[7-methyl-2-(naphthalene-1-carbonyl)-1,2,3,4-tetrahydro-pyrido[4,3-b]indol-5-yl]-acetic acid;
[8-methyl-2-(naphthalene-1-carbonyl)-1,2,3,4-tetrahydro-pyrido[4,3-b]indol-5-yl]-acetic acid;
[8-bromo-2-(naphthalene-1-carbonyl)-1,2,3,4-tetrahydro-pyrido[4,3-b]indol-5-yl]-acetic acid;
[8-fluoro-2-(naphthalene-1-carbonyl)-1,2,3,4-tetrahydro-pyrido[4,3-b]indol-5-yl]-acetic acid;
[8-fluoro-2-(2-naphthalen-1-yl-acetyl)-1,2,3,4-tetrahydro-pyrido[4,3-b]indol-5-yl]-acetic acid;
[2-(2-bromo-3-methyl-benzoyl)-7-chloro-1,2,3,4-tetrahydro-pyrido[4,3-b]indol-5-yl]-acetic acid;
[2-(2-bromo-3-methyl-benzoyl)-8-chloro-1,2,3,4-tetrahydro-pyrido[4,3-b]indol-5-yl]-acetic acid;
[2-(2-bromo-3-methyl-benzoyl)-6-chloro-1,2,3,4-tetrahydro-pyrido[4,3-b]indol-5-yl]-acetic acid;
[2-(2-bromo-3-methyl-benzoyl)-7-methyl-1,2,3,4-tetrahydro-pyrido[4,3-b]indol-5-yl]-acetic acid;
[2-(2-bromo-3-methyl-benzoyl)-8-methyl-1,2,3,4-tetrahydro-pyrido[4,3-b]indol-5-yl]-acetic acid;
[8-bromo-2-(2-bromo-3-methyl-benzoyl)-1,2,3,4-tetrahydro-pyrido[4,3-b]indol-5-yl]-acetic acid;
[2-(2-bromo-3-methyl-benzoyl)-8-fluoro-1,2,3,4-tetrahydro-pyrido[4,3-b]indol-5-yl]-acetic acid;
[8-bromo-2-(2-ethoxy-naphthalene-1-carbonyl)-1,2,3,4-tetrahydro-pyrido[4,3-b]indol-5-yl]-acetic acid;
[2-(2-ethoxy-naphthalene-1-carbonyl)-8-fluoro-1,2,3,4-tetrahydro-pyrido[4,3-b]indol-5-yl]-acetic acid;
[8-chloro-2-(2-ethoxy-naphthalene-1-carbonyl)-1,2,3,4-tetrahydro-pyrido[4,3-b]indol-5-yl]-acetic acid;
[2-(4-methoxy-naphthalene-1-carbonyl)-1,2,3,4-tetrahydro-pyrido[4,3-b]indol-5-yl]-acetic acid;
[2-(5-bromo-naphthalene-1-carbonyl)-1,2,3,4-tetrahydro-pyrido[4,3-b]indol-5-yl]-acetic acid;
[2-(4-methyl-naphthalene-1-carbonyl)-1,2,3,4-tetrahydro-pyrido[4,3-b]indol-5-yl]-acetic acid;

[2-(2-methyl-naphthalene-1-carbonyl)-1,2,3,4-tetrahydro-pyrido[4,3-b]indol-5-yl]-acetic acid;
[2-(biphenyl-3-carbonyl)-1,2,3,4-tetrahydro-pyrido[4,3-b]indol-5-yl]-acetic acid;
[2-(4-fluoro-naphthalene-1-carbonyl)-1,2,3,4-tetrahydro-pyrido[4,3-b]indol-5-yl]-acetic acid;
[2-(2-methoxy-naphthalene-1-carbonyl)-1,2,3,4-tetrahydro-pyrido[4,3-b]indol-5-yl]-acetic acid;
2-(9-oxo-9H-fluorene-2-carbonyl)-1,2,3,4-tetrahydro-pyrido[4,3-b]indol-5-yl]-acetic acid;
[2-(9H-fluorene-1-carbonyl)-1,2,3,4-tetrahydro-pyrido[4,3-b]indol-5-yl]-acetic acid;
[2-(9H-fluorene-4-carbonyl)-1,2,3,4-tetrahydro-pyrido[4,3-b]indol-5-yl]-acetic acid;
[2-(2,4,6-trifluoro-benzoyl)-1,2,3,4-tetrahydro-pyrido[4,3-b]indol-5-yl]-acetic acid;
[2-(4-cyclohexyl-benzoyl)-1,2,3,4-tetrahydro-pyrido[4,3-b]indol-5-yl]-acetic acid;
[2-(1H-indole-4-carbonyl)-1,2,3,4-tetrahydro-pyrido[4,3-b]indol-5-yl]-acetic acid;
[2-(2-fluoro-phenylcarbamoyl)-1,2,3,4-tetrahydro-pyrido[4,3-b]indol-5-yl]-acetic acid;
[2-(3-fluoro-phenylcarbamoyl)-1,2,3,4-tetrahydro-pyrido[4,3-b]indol-5-yl]-acetic acid;
[2-(4-fluoro-phenylcarbamoyl)-1,2,3,4-tetrahydro-pyrido[4,3-b]indol-5-yl]-acetic acid;
(2-o-tolylcarbamoyl-1,2,3,4-tetrahydro-pyrido[4,3-b]indol-5-yl)-acetic acid;
(2-m-tolylcarbamoyl-1,2,3,4-tetrahydro-pyrido[4,3-b]indol-5-yl)-acetic acid;
(2-p-tolylcarbamoyl-1,2,3,4-tetrahydro-pyrido[4,3-b]indol-5-yl)-acetic acid;
(2-benzylcarbamoyl-1,2,3,4-tetrahydro-pyrido[4,3-b]indol-5-yl)-acetic acid;
(2-phenethylcarbamoyl-1,2,3,4-tetrahydro-pyrido[4,3-b]indol-5-yl)-acetic acid;
[2-(naphthalen-1-ylcarbamoyl)-1,2,3,4-tetrahydro-pyrido[4,3-b]indol-5-yl]-acetic acid;
[2-(naphthalen-2-ylcarbamoyl)-1,2,3,4-tetrahydro-pyrido[4,3-b]indol-5-yl]-acetic acid;
[2-(biphenyl-2-ylcarbamoyl)-1,2,3,4-tetrahydro-pyrido[4,3-b]indol-5-yl]-acetic acid;
(2-cyclohexylcarbamoyl-1,2,3,4-tetrahydro-pyrido[4,3-b]indol-5-yl)-acetic acid;
[2-(2-chloro-phenylcarbamoyl)-1,2,3,4-tetrahydro-pyrido[4,3-b]indol-5-yl]-acetic acid;
[2-(4-fluoro-phenylthiocarbamoyl)-1,2,3,4-tetrahydro-pyrido[4,3-b]indol-5-yl]-acetic acid;
(2-phenylthiocarbamoyl-1,2,3,4-tetrahydro-pyrido[4,3-b]indol-5-yl)-acetic acid;
(2-phenethylthiocarbamoyl-1,2,3,4-tetrahydro-pyrido[4,3-b]indol-5-yl)-acetic acid;
(2-cyclohexylthiocarbamoyl-1,2,3,4-tetrahydro-pyrido[4,3-b]indol-5-yl)-acetic acid;
(2-benzylthiocarbamoyl-1,2,3,4-tetrahydro-pyrido[4,3-b]indol-5-yl)-acetic acid;
[2-(2-chloro-phenylthiocarbamoyl)-1,2,3,4-tetrahydro-pyrido[4,3-b]indol-5-yl]-acetic acid;
(2-p-tolylthiocarbamoyl-1,2,3,4-tetrahydro-pyrido[4,3-b]indol-5-yl)-acetic acid;
(2-m-tolylthiocarbamoyl-1,2,3,4-tetrahydro-pyrido[4,3-b]indol-5-yl)-acetic acid; and
(2-o-tolylthiocarbamoyl-1,2,3,4-tetrahydro-pyrido[4,3-b]indol-5-yl)-acetic acid.

A further object of the invention relates to compounds for use as a medicament, wherein said compounds are selected from the group consisting of tetrahydropyridoindole derivatives of the following general Formula (II):

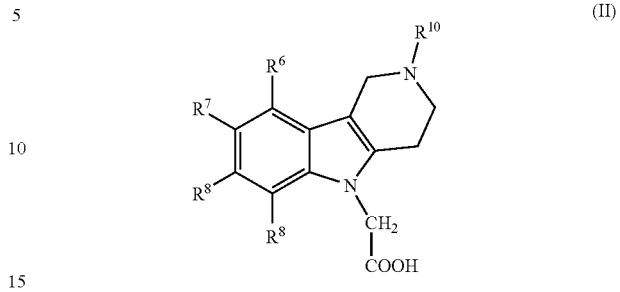

(II)

wherein $R^6$, $R^7$, $R^8$ and $R^9$ independently represent hydrogen, $C_1$-$C_5$-alkyl, $C_1$-$C_5$-alkoxy, halogen, nitro, cyano or formyl;

$R^{10}$ represents $C_0$-$C_5$-alkyl-carbonyl, $C_2$-$C_5$-alkenyl-carbonyl, $C_1$-$C_5$-alkoxy-carbonyl, $C_1$-$C_5$-alkyl, $C_1$-$C_5$-alkyl-carbamoyl, aryl-$C_1$-$C_5$-alkyl, aryl-carbonyl, aryl-$C_1$-$C_5$-alkyl-carbonyl, aryl-$C_1$-$C_5$-alkoxy-carbonyl, aryl-carbamoyl, aryl-thiocarbamoyl, aryl-$C_1$-$C_5$-alkyl-carbamoyl, aryl-$C_1$-$C_5$-alkyl-thiocarbamoyl, cycloalkyl-carbonyl, cycloalkyl-$C_1$-$C_5$-alkyl-carbonyl, cycloalkyl-$C_1$-$C_5$-alkoxy-carbonyl, cycloalkyl-carbamoyl, heteroaryl-$C_1$-$C_5$-alkyl, heteroaryl-carbonyl, heteroaryl-$C_1$-$C_5$-alkyl-carbonyl or heteroaryl-$C_1$-$C_5$-alkoxy-carbonyl;

and optically pure enantiomers, mixtures of enantiomers, racemates, optically pure diastereoisomers, mixtures of diastereoisomers, diastereoisomeric racemates, mixtures of diastereoisomeric racemates, meso forms and pharmaceutically acceptable salts thereof.

The present invention also relates to compounds of general Formula (II) for use as a medicament, wherein $R^6$, $R^7$, $R^8$ and $R^9$ independently represent hydrogen, $C_1$-$C_5$-alkyl, $C_1$-$C_5$-alkoxy, halogen, nitro, cyano or formyl; and $R^{10}$ represents $C_0$-$C_5$-alkyl-carbonyl, $C_2$-$C_5$-alkenyl-carbonyl, $C_1$-$C_5$-alkoxy-carbonyl, $C_1$-$C_5$-alkyl, $C_1$-$C_5$-alkyl-carbamoyl, aryl-$C_1$-$C_5$-alkyl, aryl-carbonyl, aryl-$C_1$-$C_5$-alkyl-carbonyl, aryl-$C_1$-$C_5$-alkoxy-carbonyl, aryl-carbamoyl, cycloalkyl-carbonyl, cycloalkyl-$C_1$-$C_5$-alkyl-carbonyl, cycloalkyl-$C_1$-$C_5$-alkoxy-carbonyl, heteroaryl-$C_1$-$C_5$-alkyl, heteroaryl-carbonyl, heteroaryl-$C_1$-$C_5$-alkyl-carbonyl or heteroaryl-$C_1$-$C_5$-alkoxy-carbonyl.

The present invention also relates to pharmaceutical compositions comprising at least one tetrahydropyridoindole derivative of the general Formula (I), or pharmaceutically acceptable salts thereof, and inert carrier materials and/or adjuvants.

The preferred embodiments described for the compounds of general Formula (I) are also preferred with regard to the pharmaceutical use of the compounds of the present invention such as their use as a medicament and their use in pharmaceutical compositions, especially for the treatment of the diseases mentioned herein.

Pharmaceutical compositions comprising at least one tetrahydropyridoindole derivative of the general Formula (II) are particularly useful for the prevention or treatment of diseases selected from the group consisting of both chronic and acute allergic/immune disorders such as allergic asthma, rhinitis, chronic obstructive pulmonary disease (COPD), dermatitis, inflammatory bowel disease, rheumatoid arthritis, allergic nephritis, conjunctivitis, atopic dermatitis, bronchial asthma, food allergy, systemic mast cell disorders, anaphylactic shock, urticaria, eczema, itching, inflammation, ischemia-reperfusion injury, cerebrovascular disorders, pleuritis, ulcerative colitis, eosinophil-related diseases, such as Churg-Strauss syndrome and sinusitis, and basophil-related diseases, such as basophilic leukemia and basophilic leukocytosis Another object of the present invention is a method for the treatment or prophylaxis of disease states mediated by CRTH2 comprising the administration to the patient of a pharmaceutically active amount of a tetrahydropyridoindole derivative according to general Formula (II).

In a preferred embodiment of the invention, said amount is comprised between 1 mg and 1000 mg per day, particularly from 2 mg to 500 mg per day, more particularly from 5 mg to 200 mg per day.

Furthermore, the present invention also concerns a process for the preparation of a pharmaceutical composition comprising at least one tetrahydropyridoindole derivative according to general Formula (II) by mixing one or more active ingredients according to general Formula (II) with inert carrier materials and/or adjuvants in a manner known per se.

The present invention also relates to the use of a tetrahydropyridoindole derivative according to general Formula (II) in the preparation of a medicament for the prevention or treatment of the diseases mentioned herein.

These pharmaceutical compositions can be administered enterally, such as orally (e.g. in the form of tablets, coated tablets, dragées, hard and soft gelatine capsules, solutions, emulsions or suspensions), nasally (e.g. in the form of nasal sprays), rectally (e.g. in the form of suppositories) or dermally. However, the administration can also be effected parenterally, such as intramuscularly or intravenously (e.g. in the form of injection solutions).

Pharmaceutical compositions comprising at least one compound of the general Formula (II) can be processed with pharmaceutically inert, inorganic or organic carrier materials and/or adjuvants for the production of tablets, coated tablets, dragées, and hard gelatine capsules. Lactose, corn starch or derivatives thereof, talc, stearic acid or its salts etc. can be used, for example, as such carrier materials or adjuvants for tablets, dragées, and hard gelatine capsules. Suitable carrier materials or adjuvants for soft gelatine capsules, are, for example, vegetable oils, waxes, fats, semi-solid substances and liquid polyols etc.

Suitable carrier materials or adjuvants for the production of solutions and syrups are, for example, water, polyols, saccharose, invert sugar, glucose etc. Suitable carrier materials or adjuvants for injection solutions are, for example, water, alcohols, polyols, glycerol, vegetable oils, etc. Suitable carrier materials or adjuvants for suppositories are, for example, natural or hardened oils, waxes, fats, semi-solid or liquid polyols, etc.

The above-described components for orally administered or injectable compositions are merely representative. Further materials as well as processing techniques and the like are set out in *Remington's Pharmaceutical Sciences*, 20th Edition, 2001, Marck Publishing Company, Easton, Pa., which is incorporated herein by reference.

These pharmaceutical compositions according to the invention can also be administered in sustained release forms or by using sustained release drug delivery systems.

A further object of the invention is a process for preparing tetrahydropyridoindole derivatives according to general Formula (I). Compounds according to general Formula (I) of the present invention are prepared according to the general sequence of reactions outlined in the schemes below, wherein $R^1$, $R^2$, $R^3$, $R^4$ and $R^5$ are as defined in general Formula (I). The compounds obtained may also be converted into a pharmaceutically acceptable salt thereof in a manner known per se.

Compounds of the invention may be manufactured by the application or adaptation of known methods, by which is meant methods used hereinafter or described in the literature, for example those described by Larock R. C. in "*Comprehensive organic transformations: a guide to functional group preparations*", VCH publishers, (1999).

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for example see Greene T. W. and Wuts P. G. M. in "*Protective groups in organic synthesis*" Wiley-Interscience (1999).

Generally, tetrahydropyridoindole derivatives of general Formula (I) are prepared as shown in Schemes 1 and 2, by condensing phenylhydrazine of Formula 1 and 4-piperidone monohydrate hydrochloride of Formula 2 in a Fischer indole synthesis to produce tetrahydropyridoindole of Formula 3, using conditions known to a skilled person (e.g. M. H. Block et al., *J. Med. Chem.* (2002), 45, 3509-3523). The nitrogen atom in Formula 3 is protected with a protecting group (PG), such as alkoxycarbonyl, preferably tert.-butoxycarbonyl, or benzyloxycarbonyl, under standard conditions, affording a compound of Formula 4. Then, compound of Formula 4 reacts with a compound of Formula L-CH$_2$CO$_2$R in which R is an alkyl group, preferably ethyl or tert.-butyl and L is a leaving group, in the presence of a base, such as caesium carbonate, sodium hydride, potassium tert.-butanolate or the like, in a suitable solvent, such as acetone, tetrahydrofuran or dioxane, to generate a compound of Formula 5. Suitable L is a leaving group such as halo, in particular bromo or chloro; mesyloxy or tosyloxy. Preferably, the compound of Formula L-CH$_2$CO$_2$R is ethyl bromo-acetate. Deprotection under standard conditions delivers an intermediate of Formula 6.

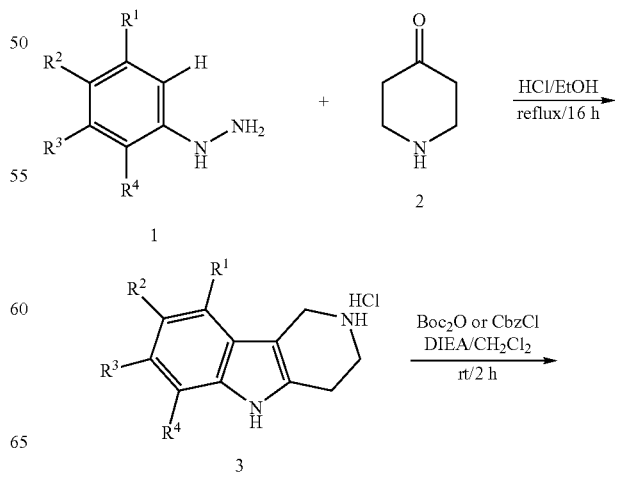

Scheme 1

-continued

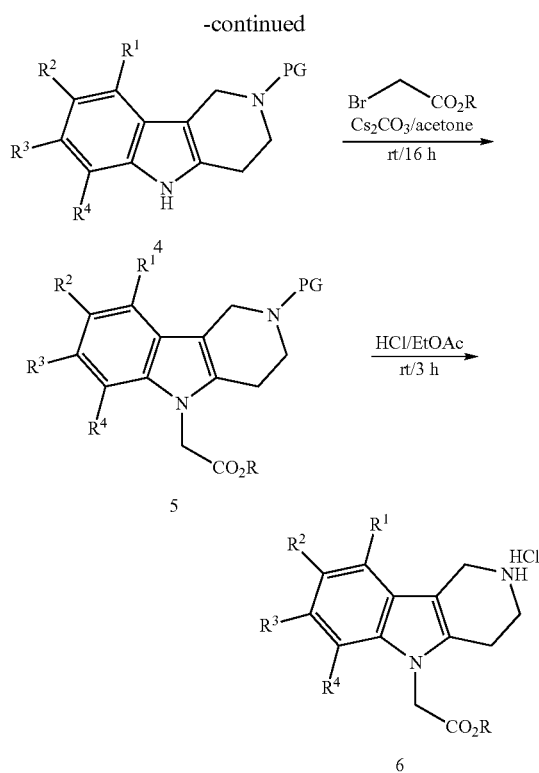

Scheme 2

Step a)

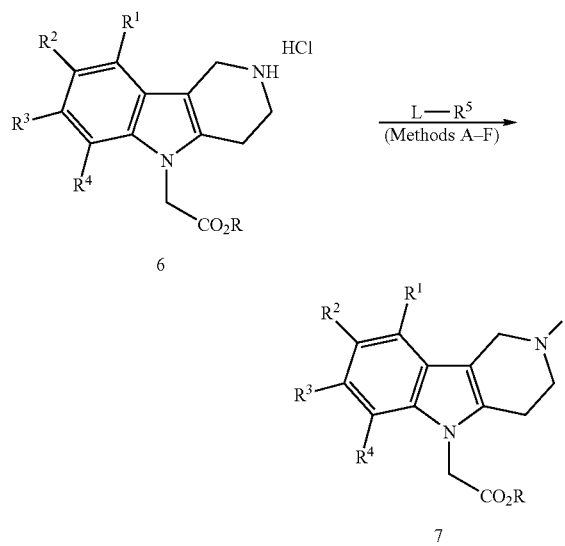

Step b)

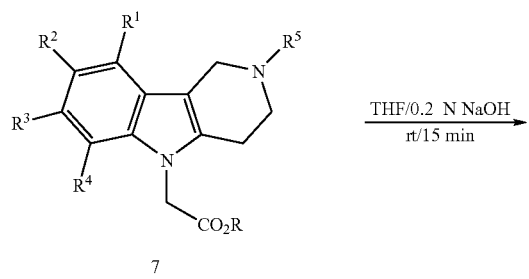

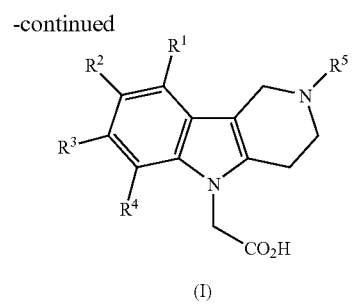

(I)

As illustrated in Scheme 2, intermediate of Formula 6 reacts in Step a) with a reagent of Formula L-$R^5$, where $R^5$ is as defined in general Formula (I) hereinabove and L is a leaving group, such as hydroxy, or halo, in particular chloro or bromo. $R^5$ transferring reagent of Formula L-$R^5$ may be a chloroformate (Method A); or an acyl halide, preferably an acid chloride, or bromide, used as such (Method B); or generated in situ from the corresponding acid with a halogenating reagent under conditions known to a skilled person, preferably by means of oxalyl chloride or phosphorous oxychloride (Method C); or an acyl anhydride, transferring $R^5$ in the presence of a base, such as triethylamine, N,N-diisopropylethylamine, N-ethyl-morpholine, N-methylpiperidine, or pyridine, in a suitable solvent, such as dichloro-methane, tetrahydrofurane, or N,N-dimethylfonnamide, to give a product of Formula 7.

In another aspect, a carboxylic acid is used in the presence of a coupling reagent (Method D), such as 1,3-dicyclohexylcarbodiimide, diisopropylcarbodiimid, O-(7-azabenzotriazol-1-yl)-N,N,N',N'-tetramethyluronium hexafluorophosphate and the like, in the presence of a base described hereinabove, to give an amide of Formula 7.

In a further aspect, isocyanates or isothiocyanates (Method E), or alkylhalides (Method F) are used in the presence of a base to form products of Formula 7.

Hydrolysis of the ester group R in Formula 7 can be carried out using routine procedures, as outlined in Scheme 2, Step b), for example by stirring with aqueous sodium hydroxide, or trifluoroacetic acid to give a compound of general Formula (I).

Alternatively, tetrahydropyridoindoles of general Formula (I) can be synthesized in three consecutive steps as outlined in Scheme 3, starting from abovementioned Fischer indole product of Formula 3, which is reacted first in a substitution reaction with abovementioned reagent of Formula L-$R^5$, using conditions as described in Methods A to F, to give a compound of Formula 8. Subsequent alkylation of the indole nitrogen can be performed with a compound of the abovementioned Formula L-$CH_2CO_2R$, in which R and L is as defined above, under conditions as described in Scheme 1 for the alkylation of compound of Formula 4, to give a precursor of Formula 7. Final deprotection under standard conditions, as outlined in Scheme 2, Step b) delivers a compound of general Formula (I).

Scheme 3

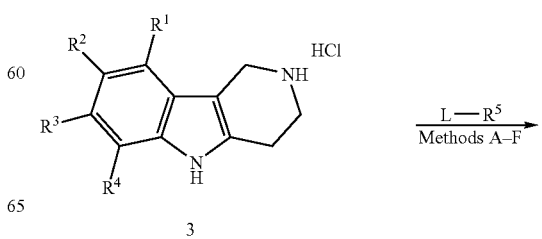

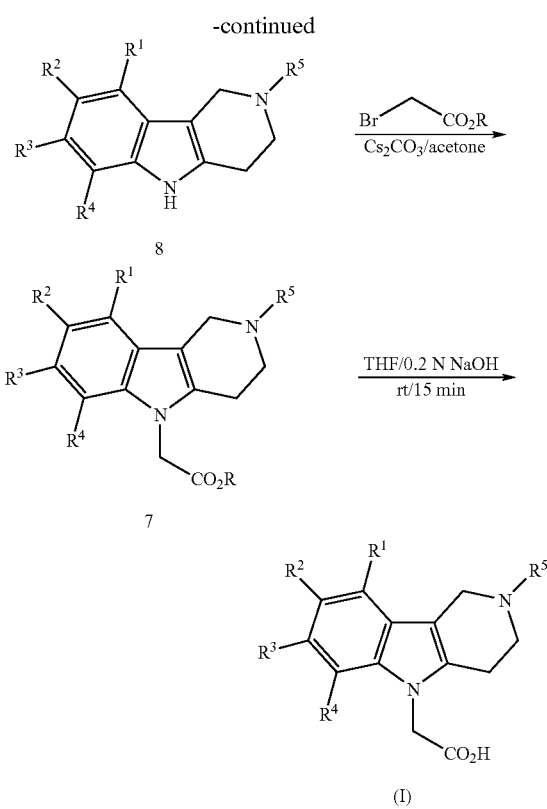

In the following the present invention shall be illustrated by means of examples, which are not construed to be viewed as limiting the scope of the invention.

Experimental Section:

Abbreviations:
AcOH acetic acid
BSA Bovine Serum Albumine
calcd calculated
$CH_2Cl_2$ dichloromethane
DIEA N,N-diisopropylethylamine
DMF Dimethylformamide
DMSO Dimethylsulfoxide
EDTA ethylenediamine tetraacetic acid
$Et_3N$ Triethylamine
ETOAc Ethyl Acetate
EtOH Ethanol
Ex. Example(s)
FLIPR Fluorescent Imaging Plate Reader
g gram
h hour
$H_2O$ water
HCl hydrochloric acid
HBSS Hank's Balanced Salt Solution
HEPES  4-(2-Hydroxyethyl)-piperazine-1-ethanesulfonic acid
HPLC High Performance Liquid Chromatography
k kilo
$K_2CO_3$ potassium carbonate
$KHSO_4$ potassium hydrogen sulfate
l liter
LC Liquid Chromatography
LDA Lithium di-isopropyl amide
MeOH Methanol
$MgCl_2$ magnesium chloride
$MgSO_4$ magnesium sulfate
µ micro
m milli
M molar
Me methyl
MeOH methanol
min minutes
mol mole
ESI-MS Electrospray Ionization Mass Spectroscopy
N Normality of solution
$NaHCO_3$ sodium hydrogenocarbonate
$NaN_3$ sodium azide
$Na_2CO_3$ sodium carbonate
NaCl sodium chloride
NaOH sodium hydroxide
$Na_2SO_4$ sodium sulfate
$NH_4OH$ ammonium acetate
PyBOP  Benzotriazole-1-yl-oxy-tris-pyrrolidino-phosphonium-hexafluorophosphate
PBS phosphate buffer saline
$PGD_2$ Prostaglandin D2
PMSF phenyl methylsulfonyl fluoride
$POCl_3$ phosphorous oxychloride
$t_R$ retention time
sat. saturated
THF Tetrahydrofuran
Tris tris-(hydroxymethyl)aminomethane buffer Chemistry General Remarks:

Temperatures are indicated in degrees Celsius (° C.). Unless otherwise indicated, the reactions take place at room temperature (rt).

In mixtures, relations of parts of solvent or eluent or reagent mixtures in liquid form are given as volume relations (v/v), unless indicated otherwise.

Analytical HPLC conditions as used in the Examples below:

LC-1: Analytical HPLC on a Xterra™ MS $C_{18}$ column (50×2.1 mm, 5 µm, Waters): Linear gradient of water/0.06% formic acid (LC-1) and acetonitrile/0.06% formic acid (B) from 5% to 95% B over 6 min; flow rate 0.25 ml/min, detection at 215 nm.

LC-2: Analytical HPLC on a GromSil MS $C_{18}$ column (50×2.1 mm, 5 µm, Waters): Linear gradient of water/0.06% formic acid (LC-1) and acetonitrile/0.06% formic acid (B) from 5% to 95% B over 6 min; flow rate 0.25 ml/min, detection at 215 nm.

LC-3: Analytical HPLC on a Waters Xterra™ MS C18 column (4.6×50 mm, 5 mm): Linear gradient of water/0.06% formic acid (A) and acetonitrile/0.06% formic acid (B) from 5% to 95% B over 1 min; flow rate 3 ml/min.

LC-4: Analytical HPLC on a Zorbax SB-AQ column (4.6×50 mm, 5 mm): Linear gradient of water/0.06% formic acid (A) and acetonitrile/0.06% formic acid (B) from 5% to 95% B over 1 min; flow rate 3 ml/min.

LC-5: Analytical HPLC on a Zorbax SB-AQ column (50×4.6 mm, 5 mm, Agilent 1100 equipped with a binary pump Dionex P580, a Photodiode Array Detector Dionex PDA-100 and a mass spectrometer Finnigan AQA): Linear gradient of water/0.04% TFA (A) and acetonitrile (B) from 5% to 95% B over 1 min; flow rate 4.5 ml/min, detection at 210, 220, 230, 254 and 280 nm.

LC-6: Analytical HPLC on a Waters Xterra™ MS C18 column (2.1×50 mm, 5 mm): Linear gradient of water/

0.06% formic acid (A) and acetonitrile/0.06%/o formic acid (B) from 5% to 95% B over 2 min; flow rate 0.75 ml/min.

Preparation of 1,2,3,4-tetrahydro-pyrido[4,3-b]indole (Intermediates of Formula 6)

Intermediate 1: Ethyl (1,2,3,4-tetrahydro-pyrido[4,3-b]indol-5-yl)-acetate hydrochloride A solution of ethyl (2-tert.-butoxycarbonyl-1,2,3,4-tetrahydro-pyrido[4,3-b]indol-5-yl)-acetate (8.45 g, 23.6 mmol) in ethyl acetate (80 ml) is treated with a solution of 3M HCl in ethyl acetate (39.3 ml). After stirring at room temperature for 3 h, the solvent is removed in vacuo and the residue azeotroped twice with toluene. The crude product is suspended in diethyl ether, filtered off, washed with diethyl ether and dried. Finally, pure title compound is obtained as beige solid (5.49 g) in 79% yield. $t_R$ (LC-2) 1.41 min; ESL-MS (positive ion): m/z 259.33 [M+H]$^+$ (calcd 258.32 for $C_{15}H_{18}N_2O_2$).

1a) 2,3,4,5-Tetrahydro-1H-pyrido[4,3-b]indole hydrochloride:

4-Piperidone monohydrate hydrochloride (10 g, 65.1 mmol) and phenylhydrazine hydrochloride (9.4 g, 65.1 mmol) are suspended in ethanol (200 ml) and stirred at reflux overnight. The resulting solid is filtered off and washed with diethyl ether to afford pure sub-title compound (11.9 g) in 88% yield. $t_R$ (LC-2) 0.89; ESI-MS (positive ion): m/z 173.34 [M+H]$^+$ (calcd 172.23 for $C_{11}H_{12}N_2$).

1b) 2-tert.-Butoxycarbonyl-1,2,3,4-tetrahydro-pyrido[4,3-b]indole:

A solution of di-tert.-butyl-dicarbonate (7.3 ml, 35.2 mmol) in dry dichloromethane (100 ml) is added to a mixture of 2,3,4,5-tetrahydro-1H-pyrido[4,3-b]indole hydrochloride (7.0 g, 33.5 mmol) and DIEA (20 ml, 117 mmol) in dry dichloromethane (200 ml). After stirring at rt for 2 h, water (100 ml) and 2N aqueous KHSO$_4$ solution (60 ml) are added. The organic layer is separated and washed successively with water and brine, dried over Mg$_2$SO$_4$, filtered and evaporated, affording crude sub-title compound as yellow oil, which solidified upon standing and is used in the next step without further purification. $t_R$ (LC-2) 2.31 min; ESI-MS (positive ion): m/z 295.37 [M+Na]$^+$ (calcd 272.34 for $C_{16}H_{20}N_2O_2$).

1c) Ethyl (2-tert.-butoxycarbonyl-1,2,3,4-tetrahydro-pyrido [4,3-b]indol-5-yl)-acetate To a stirred suspension of crude 2-tert.-butoxycarbonyl-1, 2,3,4-tetrahydro-pyrido[4,3-b]indol (33.5 mmol) and caesium carbonate (25.1 g, 77.1 mmol) in dry acetone is added ethyl bromoacetate (5.6 ml, 50.3 mmol). The reaction mixture is stirred at rt overnight and then filtered over a small plug of Celite. The filtrate is concentrated under reduced pressure and the residue is purified by silica gel column chromatography (hexane/EtOAc 5:1) to afford pure sub-title compound as yellow oil (8.45 g) in 70% yield (over two steps). $t_R$ (LC-2) 2.46 min; ESI-MS (positive ion): m/z 381.54 [M+Na]$^+$ (calcd 358.43 for $C_{20}H_{26}N_2O_4$).

Intermediate 2: Ethyl (8-bromo-1,2,3,4-tetrahydro-pyrido[4, 3-b]indol-5-yl)-acetate hydrochloride The title compound is prepared using a procedure analogous to Intermediate 1, substituting 4-bromophenylhydrazine for phenylhydrazine in Step 1a).

Intermediate 3: Ethyl (8-methyl-1,2,3,4-tetrahydro-pyrido[4, 3-b]indol-5-yl)-acetate hydrochloride The title compound is prepared using a procedure analogous to Intermediate 1, substituting 4-methylphenylhydrazine for phenylhydrazine in Step 1a).

Intermediate 4: Ethyl (7-methyl-1,2,3,4-tetrahydro-pyrido[4, 3-b]indol-5-yl)-acetate hydrochloride The title compound is prepared using a procedure analogous to Intermediate 1, substituting 3-methylphenylhydrazine for phenylhydrazine in Step 1a).

Intermediate 5: Ethyl (7-chloro-1,2,3,4-tetrahydro-pyrido[4, 3-b]indol-5-yl)-acetate hydrochloride The title compound is prepared using a procedure analogous to Intermediate 1, substituting 3-chlorophenylhydrazine for phenylhydrazine in Step 1a).

Intermediate 6: Ethyl (8-chloro-1,2,3,4-tetrahydro-pyrido[4, 3-b]indol-5-yl)-acetate hydrochloride The title compound is prepared using a procedure analogous to Intermediate 1, substituting 4-chlorophenylhydrazine for phenylhydrazine in Step 1a).

Intermediate 7: Ethyl (6-chloro-1,2,3,4-tetrahydro-pyrido[4, 3-b]indol-5-yl)-acetate hydrochloride The title compound is prepared using a procedure analogous to Intermediate 1, substituting 2-chlorophenylhydrazine for phenylhydrazine in Step 1a).

Intermediate 8: Ethyl (8-fluoro-1,2,3,4-tetrahydro-pyrido[4, 3-b]indol-5-yl)-acetate hydrochloride The title compound is prepared using a procedure analogous to Intermediate 1, substituting 4-fluorophenylhydrazine for phenylhydrazine in Step 1a).

Intermediate 9: Ethyl (6-methyl-1,2,3,4-tetrahydro-pyrido[4, 3-b]indol-5-yl)-acetate hydrochloride The title compound is prepared using a procedure analogous to Intermediate 1, substituting 2-methylphenylhydrazine for phenylhydrazine in Step 1a).

Intermediate 10: Ethyl (7-fluoro-1,2,3,4-tetrahydro-pyrido [4,3-b]indol-5-yl)-acetate hydrochloride The title compound is prepared using a procedure analogous to Intermediate 1, substituting 3-fluorophenylhydrazine for phenylhydrazine in Step 1a).

Intermediate 11: Ethyl (7,8-dichloro-1,2,3,4-tetrahydro-pyrido[4,3-b]indol-5-yl)-acetate hydrochloride The title compound is prepared using a procedure analogous to Intermediate 1, substituting 3,4-dichlorophenylhydrazine for phenylhydrazine in Step 1a).

Intermediate 12: Ethyl (8-trifluoromethyl-1,2,3,4-tetrahydro-pyrido[4,3-b]indol-5-yl)-acetate hydrochloride The title compound is prepared using a procedure analogous to Intermediate 1, substituting 4-trifluoromethylhydrazine for phenylhydrazine in Step 1a).

Intermediate 13: Ethyl (8-tert-butyl-1,2,3,4-tetrahydro-pyrido[4,3-b]indol-5-yl)-acetate hydrochloride The title compound is prepared using a procedure analogous to Intermediate 1, substituting 4-tert-butylhydrazine for phenylhydrazine in Step 1a).

Intermediate 14: Ethyl (7-Chloro-8-methyl-1,2,3,4-tetrahydro-pyrido[4,3-b]indol-5-yl)-acetate hydrochloride The title compound is prepared using a procedure analogous to Intermediate 1, substituting 3-chloro-4-methylhydrazine for phenylhydrazine in Step 1a).

Intermediate 15: Ethyl (7,8-dimethyl-1,2,3,4-tetrahydro-pyrido[4,3-b]indol-5-yl)-acetate hydrochloride The title compound is prepared using a procedure analogous to Intermediate 1, substituting 3,4-dimethylhydrazine for phenylhydrazine in Step 1a).

Intermediate 16: Ethyl (8-isopropyl-1,2,3,4-tetrahydro-pyrido[4,3-b]indol-5-yl)-acetate hydrochloride The title compound is prepared using a procedure analogous to Intermediate 1, substituting 4-isopropylhydrazine for phenylhydrazine in Step 1a).

Intermediate 17: Ethyl (3-methoxy-1,2,3,4-tetrahydro-pyrido[4,3-b]indol-5-yl)-acetate hydrochloride The title compound is prepared using a procedure analogous to Intermediate 1, substituting 3-chloro-4-methylhydrazine for phenylhydrazine in Step 1a).

EXAMPLE 1

(2-tert.-Butoxycarbonyl-1,2,3,4-tetrahydro-pyrido[4,3-b]indol-5-yl)-acetic acid

A stirred solution of ethyl (2-tert.-butoxycarbonyl-1,2,3,4-tetrahydro-pyrido[4,3-b]indol-5-yl)-acetate (15 mg, 0.039 mmol) in THF (0.6 ml) is treated with 0.2 N aqueous NaOH (0.29 ml, 0.058 mmol) at rt for 15 min. The reaction mixture is diluted with water (2 ml) and washed with diethyl ether (2 ml), then neutralized with conc. HCl (58 µl), and extracted with dichloromethane. The solvent is evaporated and the crude product is recrystallized from acetonitrile to afford pure compound as a yellow solid: $t_R$ (LC-1) 2.16 min; ESI-MS (positive ion): m/z 353.32 [M+Na]$^+$ (calcd 330.38 for $C_{18}H_{22}N_2O_4$).

EXAMPLE 2

(2-Benzyloxycarbonyl-1,2,3,4-tetrahydro-pyrido[4,3-b]indol-5-yl)-acetic acid (Method A)

To a stirred solution of Intermediate 1 (29.5 mg, 0.10 mmol) and DIEA (51 µl, 0.30 mmol) in dichloromethane (1 ml) is added benzyl chloroformate (16 µl, 0.11 mmol). The reaction mixture is stirred at rt for 1 h, 1 N aqueous HCl (2 ml). The aqueous layer is extracted twice with dichloromethane. The combined organic layers are washed with water, saturated NaHCO$_3$ solution, then are concentrated to dryness to afford crude ethyl (2-benzyloxycarbonyl-1,2,3,4-tetrahydro-pyrido[4,3-b]indol-5-yl)-acetate: $t_R$ (LC-1) 2.52 min; ESI-MS (positive ion): m/z 393.19 [M]$^+$ (calcd 392.45 for $C_{23}H_{24}N_2O_4$).

The title compound is obtained using conditions for the hydrolysis of the above crude analogous to Example 1: $t_R$ (LC-1) 2.22 min; ESI-MS (positive ion): m/z 387.14 [M+Na]$^+$ (calcd 364.40 for $C_{21}H_{20}N_2O_4$).

Examples 3-5 of the following Table 1 are prepared using a procedure analogous to that described for Example 2, substituting the appropriate chloroformates for benzyl chloroformate.

TABLE 1

| Ex. | Name | Mol Formula Mol Weight | $t_R$ [min] (Methode) | MS Data m/z [M + H]$^+$ |
|---|---|---|---|---|
| 3 | (2-butoxycarbonyl-1,2,3,4-tetrahydro-pyrido[4,3-b]indol-5-yl)-acetic acid | C18H22N2O4 330.38 | 2.22 (LC-1) | 331.22 |
| 4 | (2-ethoxycarbonyl-1,2,3,4-tetrahydro-pyrido[4,3-b]indol-5-yl)-acetic acid | C16H18N2O4 302.33 | 1.95 (LC-1) | 303.33 |
| 5 | (2-9H-fluoren-9-ylmethoxycarbonyl-1,2,3,4-tetrahydro-pyrido[4,3-b]indol-5-yl)-acetic acid | C28H24N2O4 452.51 | 2.46 (LC-1) | 453.21 |

EXAMPLE 6

[2-(Naphthalene-1-carbonyl)-1,2,3,4-tetrahydro-pyrido[4,3-b]indol-5-yl]-acetic acid (Method B)

Step a): To a stirred solution of Intermediate 1 (ethyl (1,2,3,4-tetrahydro-pyrido[4,3b]indol-5-yl)-acetate hydrochloride, 25.0 mg, 0.085 mmol) and DIEA (73 µl, 0.425 mmol) in dichloromethane (0.5 ml) is added naphthoyl chloride (15 mg, 0.11 mmol). The resulting yellow solution was kept stirring at rt for 1 h and then is quenched by adding saturated aqueous NaHCO$_3$ solution (2 ml). The organic layer is separated and washed with water (2 ml). After removal of the solvent, crude ethyl (2-benzoyl-1,2,3,4-tetrahydro-pyrido[4,3-b]indol-5-yl)-acetate is obtained pure as a yellow glassy solid: $t_R$ (LC-2) 2.20 min; ESI-MS (positive ion): m/z 386.31 [M+Na]$^+$ (calcd 362.42 for $C_{22}H_{22}N2O_3$).

Step b): A solution of crude ethyl (2-benzoyl-1,2,3,4-tetrahydro-pyrido[4,3-b]indol-5-yl)-acetate (0.085 mmol) in THF (0.5 ml) is treated with 0.2 N aqueous NaOH solution (0.64 ml) at rt for 15 min. Then, the yellow reaction mixture is diluted with water (2 ml), washed with diethyl ether (2 ml), acidified with conc. HCl to pH 1 and extracted with dichloromethane. The combined organic phases are washed with water, then dried over Na$_2$SO$_4$, filtered and the solvent evaporated. The crude product is recrystallized from diisopropyl ether to give pure title compound as yellow solid: $t_R$ (LC-1) 2.95 min; ESI-MS positive ion): m/z 335.17 [M+H]$^+$ (calcd 334.37 for $C_{20}H_{18}N_2O_3$).

Examples 7-31 of the following Table 2 are prepared using a procedure analogous to that described for Example 6, substituting the appropriate acid chloride for naphthoylchloride.

TABLE 2

| Ex. | Name | Mol Formula Mol Weight | $t_R$ [min] (Methode) | MS Data m/z [M + H]$^+$ |
|---|---|---|---|---|
| 7 | (2-acetyl-1,2,3,4-tetrahydro-pyrido[4,3-b]indol-5-yl)-acetic acid | C15H16N2O3 272.30 | 1.65 (LC-2) | 273.21 |
| 8 | (2-phenylacetyl-1,2,3,4-tetrahydro-pyrido[4,3-b]indol-5-yl)-acetic acid | C21H20N2O3 348.40 | 1.97 (LC-1) | 349.37 |

TABLE 2-continued

| Ex. | Name | Mol Formula Mol Weight | t$_R$ [min] (Methode) | MS Data m/z [M + H]$^+$ |
|---|---|---|---|---|
| 9 | (2-benzoyl-1,2,3,4-tetrahydro-pyrido[4,3-b]indol-5-yl)-acetic acid | C20H18N2O3 334.37 | 1.95 (LC-1) | 335.17 |
| 10 | [2-(3,4,5-trimethoxy-benzoyl)-1,2,3,4-tetrahydro-pyrido[4,3-b]indol-5-yl]-acetic acid | C23H24N2O6 424.45 | 1.92 (LC-1) | 425.17 |
| 11 | (2-cyclohexanecarbony-1,2,3,4-tetrahydro-pyrido[4,3-b]indol-5-yl)-acetic acid | C20H24N2O3 340.42 | 2.08 (LC-1) | 341.22 |
| 12 | [2-(4-methoxy-benzoyl)-1,2,3,4-tetrahydro-pyrido[4,3-b]indol-5-yl]-acetic acid | C21H20N2O4 364.40 | 1.96 (LC-1) | 365.17 |
| 13 | [2-(thiophene-2-carbonyl)-1,2,3,4-tetrahydro-pyrido[4,3-b]indol-5-yl]-acetic acid | C18H16N2O3S 340.40 | 1.94 (LC-1) | 341.09 |
| 14 | [2-(furan-2-carbonyl)-1,2,3,4-tetrahydro-pyrido[4,3-b]indol-5-yl]-acetic acid | C18H16N2O4 324.34 | 1.86 (LC-1) | 325.11 |
| 15 | (2-cyclopropanecarbonyl-1,2,3,4-tetrahydro-pyrido[4,3-b]indol-5-yl)-acetic acid | C17H18N2O3 298.34 | 1.82 (LC-1) | 299.12 |
| 16 | [2-(2-methoxy-benzoyl)-1,2,3,4-tetrahydro-pyrido[4,3-b]indol-5-yl]-acetic acid | C21H20N2O4 364.40 | 1.94 (LC-1) | 365.17 |
| 17 | [2-(4-trifluoromethyl-benzoyl)-1,2,3,4-tetrahydro-pyrido[4,3-b]indol-5-yl]-acetic acid | C21H17N2O3F3 402.37 | 2.16 (LC-1) | 403.13 |
| 18 | [2-(3,5-bis-trifluoromethyl-benzoyl)-1,2,3,4-tetrahydro-pyrido[4,3-b]indol-5-yl]-acetic acid | C22H16N2O3F6 470.37 | 2.34 (LC-1) | 471.11 |
| 19 | [2-(3-cyclopentyl-propionyl)-1,2,3,4-tetrahydro-pyrido[4,3-b]indol-5-yl]-acetic acid | C21H26N2O3 354.45 | 2.22 (LC-1) | 355.17 |
| 20 | [2-(3-phenyl-propionyl)-1,2,3,4-tetrahydro-pyrido[4,3-b]indol-5-yl]-acetic acid | C22H22N2O3 362.43 | 2.09 (LC-1) | 363.19 |
| 21 | [2-(biphenyl-4-carbonyl)-1,2,3,4-tetrahydro-pyrido[4,3-b]indol-5-yl]-acetic acid | C26H22N2O3 410.47 | 2.26 (LC-1) | 411.16 |
| 22 | [2-(4-tert-butyl-benzoyl)-1,2,3,4-tetrahydro-pyrido[4,3-b]indol-5-yl]-acetic acid | C24H26N2O3 390.48 | 2.29 (LC-1) | 391.22 |
| 23 | [2-(4-trifluoromethoxy-benzoyl)-1,2,3,4-tetrahydro-pyrido[4,3-b]indol-5-yl]-acetic acid | C21H17N2O4F3 418.37 | 2.20 (LC-1) | 419.06 |
| 24 | [2-((E)-but-2-enoyl)-1,2,3,4-tetrahydro-pyrido[4,3-b]indol-5-yl]-acetic acid | C17H18N2O3 298.34 | 1.82 (LC-1) | 299.12 |
| 25 | [2-(4-chloro-benzoyl)-1,2,3,4-tetrahydro-pyrido[4,3-b]indol-5-yl]-acetic acid | C20H17N2O3Cl 368.82 | 2.10 (LC-1) | 369.12 |
| 26 | [2-(3,5-dimethoxy-benzoyl)-1,2,3,4-tetrahydro-pyrido[4,3-b]indol-5-yl]-acetic acid | C22H22N2O5 394.43 | 2.01 (LC-1) | 395.17 |
| 27 | (2-diphenylacetyl-1,2,3,4-tetrahydro-pyrido[4,3-b]indol-5-yl)-acetic acid | C27H24N2O3 424.50 | 2.27 (LC-1) | 425.17 |
| 28 | (2-hexanoyl-1,2,3,4-tetrahydro-pyrido[4,3-b]indol-5-yl)-acetic acid | C19H24N2O3 328.41 | 2.10 (LC-1) | 329.25 |
| 29 | [2-(3-chloro-benzoyl)-1,2,3,4-tetrahydro-pyrido[4,3-b]indol-5-yl]-acetic acid | C20H17N2O3Cl 368.82 | 2.08 (LC-1) | 369.12 |
| 30 | [2-(4-bromo-benzoyl)-1,2,3,4-tetrahydro-pyrido[4,3-b]indol-5-yl]-acetic acid | C20H17N2O3Br 413.27 | 2.11 (LC-1) | 415.05 |
| 31 | [2-(pyridine-3-carbonyl)-1,2,3,4-tetrahydro-pyrido[4,3-b]indol-5-yl]-acetic acid | C19H17N3O3 335.36 | 1.62 (LC-1) | 336.25 |

EXAMPLE 32

(2-Benzoyl-8-methoxy-1,2,3,4-tetrahydro-pyrido[4,3-b]-5-yl)-acetic acid

The title compound is obtained using conditions for the hydrolysis of ethyl (8-methoxy-2-phenylcarbamoyl-1,2,3,4-tetrahydro-pyrido[4,3-b]indol-5-yl)-acetate analogous to Example 1: t$_R$ (LC-1) 1.92; ESI-MS (positive ion): m/z 364.23 [M]$^+$ (calcd 364.39 for C$_{21}$H$_{20}$N$_2$O$_4$).

32a) 8-Methoxy-2,3,4,5-tetrahydro-1H-pyrido[4,3-b]indole

A suspension of 4-piperidone monohydrate hydrochloride (1.0 g, 6.5 mmol) and 4-methoxyphenylhydrazine hydrochloride (1.14 g, 6.5 mmol) in ethanol (17 ml) is kept stirring at reflux overnight. The resulting solid is filtered off and washed with diethyl ether to afford crude sub-title compound, which is used without further purification: t$_R$ (LC-1) 0.38; ESI-MS (positive ion): m/z 203.19 [M+H]$^+$ (calcd 202.25 for C$_{12}$H$_{14}$N$_2$O).

32b) 8-Methoxy-1,3,4,5-tetrahydro-pyrido[4,3-b]indole-2-carboxylic acid phenylamide The subtitle compound is prepared using Method B as described for Example 6, substituting 8-methoxy-2,3,4,5-tetrahydro-1H-pyrido[4,3-b]indole for Intermediate 1: t$_R$ (LC-1) 2.03; ESI-MS (positive ion): m/z 307.21 [M+H]$^+$ (calcd 306.36 for C$_{19}$H$_{18}$N$_2$O$_2$).

32c) Ethyl (8-methoxy-2-phenylcarbamoyl-1,2,3,4-tetrahydro-pyrido[4,3-b]indol-5-yl)-acetate The subtitle compound is prepared according to Step 1c) in the procedure described for the synthesis of Intermediate 1, substituting 8-methoxy-1,3,4,5-tetrahydro-pyrido[4,3-b]indole-2-carboxylic acid phenylamide for 2-tert.-butoxycarbonyl-1,2,3,4-tetrahydro-pyrido[4,3-b]indole: $t_R$ (LC-1) 2.21 min; ESI-MS (positive ion): m/z 393.32 [M+H]$^+$ (calcd 392.17 for $C_{23}H_{24}N_2O_4$).

Examples 33-36 of the following Table 3 are prepared using a procedure analogous to that described for Example 32, substituting the appropriate phenylhydrazine for 4-methoxyphenylhydrazine.

TABLE 3

| Ex. | Name | Mol Formula Mol Weight | $t_R$ [min] (Methode) | MS Data m/z [M + H]$^+$ |
|---|---|---|---|---|
| 33 | (2-benzoyl-7-methyl-1,2,3,4-tetrahydro-pyrido[4,3-b]indol-5-yl)-acetic acid | C21H20N2O3 348.40 | 2.03 (LC-1) | 349.24 |
| 34 | (2-benzoyl-8-bromo-1,2,3,4-tetrahydro-pyrido[4,3-b]indol-5-yl)-acetic acid | C20H17BrN2O3 413.26 | 2.11 (LC-1) | 413.13 |
| 35 | (2-benzoyl-8-methyl-1,2,3,4-tetrahydro-pyrido[4,3-b]indol-5-yl)-acetic acid | C21H20N2O3 348.40 | 2.05 (LC-1) | 349.18 |
| 36 | (2-benzoyl-6-methyl-1,2,3,4-tetrahydro-pyrido[4,3-b]indol-5-yl)-acetic acid | C21H20N2O3 348.40 | 2.01 (LC-1) | 349.24 |

EXAMPLE 37

[2-(2-Cyclohexyl-2-phenyl-acetyl)-1,2,3,4-tetrahydro-pyrido[4,3-b]indol-5yl]-acetic acid (Method C)

Step a): To a stirred solution of Intermediate 1 (25 mg, 0.085 mmol), cyclohexyl-phenylacetic acid (27.7 mg, 0.127 mmol) and DIEA (73 μl, 0.424 mmol) in dichloromethane (1 ml) is added POCl$_3$ (9 μl, 0.093 mmol). The resulting yellow reaction mixture is stirred at rt overnight, then saturated aqueous NaHCO$_3$ solution (2 ml) is added. The organic layer is separated and washed with water (2 ml). Evaporation of the solvent gave a crude that is purified by silica gel column chromatography (hexane/EtOAc 3:1) affording ethyl [2-(2-cyclohexyl-2-phenyl-acetyl)-1,2,3,4-tetrahydro-pyrido[4,3-b]indol-5-yl]-acetate as a white solid (29 mg) in 74% yield: $t_R$ (LC-2) 2.74 min; ESI-MS (positive ion): m/z 459.25 [M+H]$^+$ (calcd 458.59 for $C_{29}H_{34}N_2O_3$).

Step b): The title compound is obtained using conditions for the hydrolysis of the above analogous to Example 1: $t_R$ (LC-2) 2.47 min; ESI-MS (positive ion): m/z 431.22 [M+H]$^+$ (calcd 430.55 for $C_{27}H_{30}N_2O_3$).

Example 38-52 of the following Table 4 are prepared using a procedure analogous to that described for Example 37, substituting the appropriate acid for cyclohexylphenylacetic acid.

TABLE 4

| Ex. | Name | Mol Formula Mol Weight | $t_R$ [min] (Methode) | MS Data m/z [M + H]$^+$ |
|---|---|---|---|---|
| 38 | [2-(pyrazine-2-carbonyl)-1,2,3,4-tetrahydro-pyrido[4,3-b]indol-5-yl]-acetic acid | C18H16N4O3 336.35 | 1.80 (LC-1) | 337.14 |
| 39 | [2-(4'-ethyl-biphenyl-4-carbonyl)-1,2,3,4-tetrahydro-pyrido[4,3-b]indol-5-yl]-acetic acid | C28H26N2O3 438.53 | 2.50 (LC-1) | 439.18 |
| 40 | [2-(2-bromo-3-methyl-benzoyl)-1,2,3,4-tetrahydro-pyrido[4,3-b]indol-5-yl]-acetic acid | C21H19N2O3Br 427.30 | 2.15 (LC-1) | 429.05 |
| 41 | [2-(2-bromo-5-methyl-benzoyl)-1,2,3,4-tetrahydro-pyrido[4,3-b]indol-5-yl]-acetic acid | C21H19N2O3Br 427.30 | 2.17 (LC-1) | 429.05 |
| 42 | [2-(2-chloro-6-methyl-pyridine-4-carbonyl)-1,2,3,4-tetrahydro-pyrido[4,3-b]indol-5-yl]-acetic acid | C20H18N3O3Cl 383.83 | 2.00 (LC-1) | 384.08 |
| 43 | [2-(biphenyl-2-carbonyl)-1,2,3,4-tetrahydro-pyrido[4,3-b]indol-5-yl]-acetic acid | C26H22N2O3 410.47 | 2.23 (LC-1) | 411.15 |
| 44 | [2-(5-bromo-furan-2-carbonyl)-1,2,3,4-tetrahydro-pyrido[4,3-b]indol-5-yl]-acetic acid | C18H15N2O4Br 403.23 | 2.10 (LC-1) | 403.00 |
| 45 | [2-(3-methyl-furan-2-carbonyl)-1,2,3,4-tetrahydro-pyrido[4,3-b]indol-5-yl]-acetic acid | C19H18N2O4 338.36 | 2.01 (LC-1) | 339.12 |
| 46 | [2-(2-methyl-furan-3-carbonyl)-1,2,3,4-tetrahydro-pyrido[4,3-b]indol-5-yl]-acetic acid | C19H18N2O4 338.36 | 1.97 (LC-1) | 339.18 |
| 47 | [2-(benzo[b]thiophene-2-carbonyl)-1,2,3,4-tetrahydro-pyrido[4,3-b]indol-5-yl]-acetic acid | C22H18N2O3S 390.46 | 2.23 (LC-1) | 391.09 |
| 48 | [2-(5-chloro-thiophene-2-carbonyl)-1,2,3,4-tetrahydro-pyrido[4,3-b]indol-5-yl]-acetic acid | C18H15N2O3ClS 374.85 | 2.20 (LC-1) | 375.04 |
| 49 | [2-(furan-3-carbonyl)-1,2,3,4-tetrahydro-pyrido[4,3-b]indol-5-yl]-acetic acid | C18H16N2O4 324.34 | 1.89 (LC-1) | 325.17 |
| 50 | [2-(2-naphthalen-2-yl-acetyl)-1,2,3,4-tetrahydro-pyrido[4,3-b]indol-5-yl]-acetic acid | C25H22N2O3 398.46 | 2.23 (LC-1) | 399.18 |
| 51 | [2-(thiophene-3-carbonyl)-1,2,3,4-tetrahydro-pyrido[4,3-b]indol-5-yl]-acetic acid | C18H16N2O3S 340.40 | 1.96 (LC-1) | 341.09 |
| 52 | [2-(2-naphthalen-1-yl-acetyl)-1,2,3,4-tetrahydro-pyrido[4,3-b]indol-5-yl]-acetic acid | C25H22N2O3 398.46 | 2.24 (LC-1) | 399.18 |

EXAMPLE 53

[2-(2-Ethoxy-naphthalene-1-carbonyl)-1,2,3,4-tetrahydro-pyrido[4,3-b]indol-5yl]-acetic acid (Method D)

Step a): To a solution of 2-ethoxynaphthoic acid (22 mg, 0.1 mmol), N',N',N',N'tetramethyl-O-(7-azabenzotriazole-1-yl)-uronium-hexafluorophosphate (38 mg, 0.1 mmol) and DIEA (51 μl, 0.3 mmol) in THF/DMF (4:1, 1 ml) is added Intermediate 1 (29 mg, 0.1 mmol) in one portion and the reaction mixture is stirred at rt overnight. Then, the solvent is evaporated and the residue purified by silica gel column chromatography (6% MeOH in $CH_2Cl_2$/aqueous $NH_4OH$ 9:1) affording ethyl [2-(2-ethoxy-naphthalene-1-carbonyl)-1,2,3,4-tetrahydro-pyrido[4,3-b]indol-5-yl]-acetate (43 mg) as a glassy brown solid in 93% yield.

Step b): The title compound is obtained using conditions for the hydrolysis of the above ester analogous to Example 1: $t_R$ (LC-2) 2.49 min; ESI-MS positive ion): m/z 429.24 $[M+H]^+$ (calcd 428.48 for $C_{26}H_{24}N_2O_4$).

Examples 54-56 of the following Table 5 are prepared using a procedure analogous to that described for Example 53, substituting the appropriate acid for 2-ethoxynaphthoic acid.

TABLE 5

| Ex. | Name | Mol Formula Mol Weight | $t_R$ [min] (Methode) | MS Data m/z $[M + H]^+$ |
|---|---|---|---|---|
| 54 | [2-(3-methyl-thiophene-2-carbonyl)-1,2,3,4-tetrahydro-pyrido[4,3-b]indol-5-yl]-acetic acid | C19H18N2O3S 354.43 | 2.33 (LC-2) | 355.23 |
| 55 | [2-(5-methyl-thiophene-2-carbonyl)-1,2,3,4-tetrahydro-pyrido[4,3-b]indol-5-yl]-acetic acid | C19H18N2O3S 354.43 | 2.38 (LC-2) | 355.23 |
| 56 | [2-(pyridine-4-carbonyl)-1,2,3,4-tetrahydro-pyrido[4,3-b]indol-5-yl]-acetic acid | C19H17N3O3 335.36 | 1.90 (LC-2) | 336.25 |

EXAMPLE 57

(2-Phenylcarbamoyl-1,2,3,4-tetrahydro-pyrido[4,3-b]indol-5-yl)-acetic acid (Method E)

Step a): To a stirred solution of Intermediate 1 (20 mg, 0.068 mnol) and DIEA (35 μl, 0.20 mmol) in dichloromethane (1 ml) is added phenyl isocyanate (8.2 μl, 0.075 mmol). The reaction mixture is kept stirring at rt for 1 h, then 1N HCl (2 ml) was added. The aqueous layer is extracted twice with dichloromethane. The organic layers are combined and the solvent is evaporated to give crude ethyl (2-phenylcarbamoyl-1,2,3,4-tetrahydro-pyrido[4,3-b]indol-5-yl)-acetic acid: $t_R$ (LC-2) 2.23 min; ESI-MS (positive ion): m/z 400.39 $[M+Na]^+$ (calcd 377.44 for $C_{22}H_{23}N_3O_3$); $^1$H-NMR ($CDCl_3$): 1.19 (t, J=7.0 Hz, 3H); 2.77 (t, J=5.3 Hz, 2H); 3.91 (t, J=5.3 Hz, 2H); 4.14 (q, J=7.0 Hz, 2H); 4.65 (s, 2H); 4.68 (s, 2H); 6.46 (s, 1H); 6.98 (t, J=7.0 Hz, 1H); 7.04-7.09 (m, 1H); 7.14-7.16 (m, 2H); 7.20-7.26 (m, 2H); 7.32-7.35 (m, 2H); 7.40 (d, J=7.6 Hz, 1H).

Step b): The title compound is obtained using conditions for the hydrolysis of the above crude analogous to Example 1: $t_R$ (LC-2) 1.95 min; ESI-MS (positive ion): m/z 350.26 $[M+H]^+$ (calcd 349.39 for $C_{20}H_{19}N_3O_3$); $^1$H-NMR (DMSO-$D_6$): 2.77 (m, 2H); 3.83 (t, J=5.3 Hz, 2H); 4.67 (s, 2H); 4.91 (s, 2H); 6.91 (t, J=7.0 Hz, 1H); 6.99-7.10 (m, 2H); 7.19-7.24 (m, 2H); 7.35-7.47 (m, 4H); 8.64 (s, 1H); 13.0 (br s, 1H).

EXAMPLE 58

(2-Ethylcarbamoyl-1,2,3,4-tetrahydro-pyrido[4,3-b]indol-5-yl)-acetic acid

The title compound is prepared using a procedure analogous to Example 57, substituting ethyl isocyanate for phenyl isocyanate: $t_R$ (LC-2) 1.68 min; ESI-MS (positive ion): 7 m/z 302.24 $[M+H]^+$ (calcd 301.35 for $C_{16}H_{19}N_3O_3$).

EXAMPLE 59

(2-Phenethyl-1,2,3,4-tetrahydro-pyrido[4,3-b]indol-5-yl)-acetate, sodium salt (Method F)

Step a): To a stirred solution of Intermediate 1 (50 mg, 0.17 mmol) and DIEA (73 μl, 0.42 mmol) in acetonitrile (1 ml) is added (2-bromo-ethyl)-benzene (26 μl, 0.19 mmol). The reaction mixture is stirred at rt overnight. The solvent is removed under reduced pressure and the crude product is purified by silica gel column chromatography (hexane/EtOAc 3:1, 1% $NEt_3$), affording pure ethyl (2-phenethyl-1,2,3,4-tetrahydro-pyrido[4,3-b]indol-5-yl)-acetate (37 mg) in 60% yield: $t_R$ (LC-2) 1.69 min; ESI-MS (pos. ion): m/z 363.26 $[M+H]^+$ (calcd 362.46 for $C_{23}H_{26}N_2O_2$).

Step b): A stirred solution of the above ester in THF (1 ml) was treated with 0.2 N aqueous NaOH (0.51 ml, 0.10 mmol) at rt for 15 min. The yellow solution is diluted with 0.5 ml of water and washed twice with diethyl ether (2 ml each). The aqueous phase is concentrated and the precipitate filtered off, affording pure title compound (29 mg) in 79% yield: $t_R$ (LC-2) 1.55 min; ESI-MS (pos. ion): m/z 335.36 $[M+H]^+$ (calcd 334.41 for $C_{21}H_{22}N_2O_2$).

EXAMPLE 60

[2-(3-Phenyl-propyl)-1,2,3,4-tetrahydro-pyrido[4,3-b]indol-5-yl]-acetate, sodium salt The title compound is prepared using a procedure analogous to Example 59, substituting (3-bromo-propyl)-benzene for (2-bromo-ethyl)-benzene: $t_R$ (LC-2) 1.61 min; ESI-MS (positive ion): m/z 349.37 $[M+H]^+$ (calcd 348.44 for $C_{22}H_{24}N_2O_2$).

Examples 61-67 of the following Table 6 are prepared using a procedure analogous to that described for Example 1, substituting the appropriate substituted (2-tert.-butoxycarbonyl-1,2,3,4-tetrahydro-pyrido[4,3-b]indol-5-yl)-acetate for (2-tert.-butoxycarbonyl-1,2,3,4-tetrahydro-pyrido[4,3-b]indol-5-yl)-acetate.

TABLE 6

| Ex. | Name | Mol Formula Mol Weight | $t_R$ [min] (Methode) | MS Data m/z [M + H]$^+$ |
|---|---|---|---|---|
| 61 | 5-carboxymethyl-7-chloro-1,3,4,5-tetrahydro-pyrido[4,3-b]indole-2-carboxylic acid tert-butyl ester | C18H21N2O4Cl 364.828 | 1.10 (LC-4) | 363.09[M – H]$^+$ |
| 62 | 5-carboxymethyl-8-chloro-1,3,4,5-tetrahydro-pyrido[4,3-b]indole-2-carboxylic acid tert-butyl ester | C18H21N2O4Cl 364.828 | 1.10 (LC-4) | 363.09[M – H]$^+$ |
| 63 | 5-carboxymethyl-6-chloro-1,3,4,5-tetrahydro-pyrido[4,3-b]indole-2-carboxylic acid tert-butyl ester | C18H21N2O4Cl 364.828 | 1.15 (LC-4) | 363.09[M – H]$^+$ |
| 64 | 5-carboxymethyl-7-methyl-1,3,4,5-tetrahydro-pyrido[4,3-b]indole-2-carboxylic acid tert-butyl ester | C19H24N2O4 344.41 | 1.13 (LC-4) | 343.22[M – H]$^+$ |
| 65 | 5-carboxymethyl-8-methyl-1,3,4,5-tetrahydro-pyrido[4,3-b]indole-2-carboxylic acid tert-butyl ester | C19H24N2O4 344.41 | 1.14 (LC-4) | 343.08[M – H]$^+$ |
| 66 | 8-bromo-5-carboxymethyl-1,3,4,5-tetrahydro-pyrido[4,3-b]indole-2-carboxylic acid tert-butyl ester | C18H21N2O4Br 409.279 | 1.11 (LC-4) | 410.83 |
| 67 | 5-carboxymethyl-8-fluoro-1,3,4,5-tetrahydro-pyrido[4,3-b]indole-2-carboxylic acid tert-butyl ester | C18H21N2O4F 348.373 | 1.07 (LC-4) | 347.17[M – H]$^+$ |

Examples 68-96 of the following Table 7 are prepared using a procedure analogous to that described for Example 6, substituting the appropriate acid chloride for naphthoylchloride and substituting the appropriate Intermediate for Intermediate 1.

TABLE 7

| Ex. | Name | Mol Formula Mol Weight | $t_R$ [min] (Methode) | MS Data m/z [M + H]$^+$ |
|---|---|---|---|---|
| 68 | [7-chloro-2-(3-chloro-benzoyl)-1,2,3,4-tetrahydro-pyrido[4,3-b]indol-5-yl]-acetic acid | C20H16N2O3Cl2 403.264 | 1.10 (LC-4) | 402.87 [M – H]$^+$ |
| 69 | [8-chloro-2-(3-chloro-benzoyl)-1,2,3,4-tetrahydro-pyrido[4,3-b]indol-5-yl]-acetic acid | C20H16N2O3Cl2 403.264 | 1.10 (LC-4) | 402.8 [M – H]$^+$ |
| 70 | [6-chloro-2-(3-chloro-benzoyl)-1,2,3,4-tetrahydro-pyrido[4,3-b]indol-5-yl]-acetic acid | C20H16N2O3Cl2 403.264 | 1.08 (LC-4) | 402.97 [M – H]$^+$ |
| 71 | [2-(3-chloro-benzoyl)-7-methyl-1,2,3,4-tetrahydro-pyrido[4,3-b]indol-5-yl]-acetic acid | C21H19N2O3Cl 382.846 | 1.04 (LC-4) | 383.10 |
| 72 | [2-(3-chloro-benzoyl)-8-methyl-1,2,3,4-tetrahydro-pyrido[4,3-b]indol-5-yl]-acetic acid | C21H19N2O3Cl 382.846 | 1.07 (LC-4) | 382.87 [M]$^+$ |
| 73 | [8-bromo-2-(3-chloro-benzoyl)-1,2,3,4-tetrahydro-pyrido[4,3-b]indol-5-yl]-acetic acid | C20H16N2O3BrCl 447.715 | 1.11 (LC-4) | 448.83 |
| 74 | [2-(3-chloro-benzoyl)-8-fluoro-1,2,3,4-tetrahydro-pyrido[4,3-b]indol-5-yl]-acetic acid | C20H16N2O3ClF 386.809 | 1.03 (LC-4) | 385.09 [M – H]$^+$ |
| 75 | [8-chloro-2-(thiophene-2-carbonyl)-1,2,3,4-tetrahydro-pyrido[4,3-b]indol-5-yl]-acetic acid | C18H15N2O3ClS 374.847 | 1.06 (LC-4) | 373.05 [M – H]$^+$ |
| 76 | [6-chloro-2-(thiophene-2-carbonyl)-1,2,3,4-tetrahydro-pyrido[4,3-b]indol-5-yl]-acetic acid | C18H15N2O3ClS 374.847 | 1.05 (LC-4) | 375.06 |
| 77 | [8-bromo-2-(thiophene-2-carbonyl)-1,2,3,4-tetrahydro-pyrido[4,3-b]indol-5-yl]-acetic acid | C18H15N2O3BrS 419.298 | 1.08 (LC-4) | 421.01 |
| 78 | [8-fluoro-2-(thiophene-2-carbonyl)-1,2,3,4-tetrahydro-pyrido[4,3-b]indol-5-yl]-acetic acid | C18H15N2O3FS 358.392 | 1.03 (LC-4) | 359.00 |
| 79 | [7-chloro-2-(thiophene-2-carbonyl)-1,2,3,4-tetrahydro-pyrido[4,3-b]indol-5-yl]-acetic acid | C18H15N2O3ClS 374.847 | 1.01 (LC-4) | 375.00 |
| 80 | [7-methyl-2-(thiophene-2-carbonyl)-1,2,3,4-tetrahydro-pyrido[4,3-b]indol-5-yl]-acetic acid | C19H18N2O3S 354.429 | 1.01 (LC-4) | 355.06 |
| 81 | [8-methyl-2-(thiophene-2-carbonyl)-1,2,3,4-tetrahydro-pyrido[4,3-b]indol-5-yl]-acetic acid | C19H18N2O3S 354.429 | 1.04 (LC-4) | 355.06 |
| 82 | [8-fluoro-2-(2-methoxy-naphthalene-1-carbonyl)-1,2,3,4-tetrahydro-pyrido[4,3-b]indol-5-yl]-acetic acid | C25H21N2O4F 432.45 | 1.04 (LC-4) | 431.12 [M – H]$^+$ |
| 83 | [8-fluoro-2-(4-methoxy-naphthalene-1-carbonyl)-1,2,3,4-tetrahydro-pyrido[4,3-b]indol-5-yl]-acetic acid | C25H21N2O4F 432.45 | 1.05 (LC-4) | 431.12 [M – H]$^+$ |
| 84 | [8-chloro-2-(2-methoxy-naphthalene-1-carbonyl)-1,2,3,4-tetrahydro-pyrido[4,3-b]indol-5-yl]-acetic acid | C25H21N2O4Cl 448.905 | 1.07 (LC-4) | 447.04 [M – H]$^+$ |
| 85 | [8-chloro-2-(4-methoxy-naphthalene-1-carbonyl)-1,2,3,4-tetrahydro-pyrido[4,3-b]indol-5-yl]-acetic acid | C25H21N2O4Cl 448.905 | 1.08 (LC-4) | 448.82 [M]$^+$ |
| 86 | [2-(2-methoxy-naphthalene-1-carbonyl)-8-methyl-1,2,3,4-tetrahydro-pyrido[4,3-b]indol-5-yl]-acetic acid | C26H24N2O4 428.487 | 1.04 (LC-4) | 429.04 |
| 87 | [2-(4-methoxy-naphthalene-1-carbonyl)-8-methyl-1,2,3,4-tetrahydro-pyrido[4,3-b]indol-5-yl]-acetic acid | C26H24N2O4 428.487 | 1.08 (LC-4) | 429.04 |
| 88 | [2-(2-methoxy-naphthalene-1-carbonyl)-7-methyl-1,2,3,4-tetrahydro-pyrido[4,3-b]indol-5-yl]-acetic acid | C26H24N2O4 428.487 | 1.04 (LC-4) | 429.04 |
| 89 | [2-(2-ethoxy-naphthalene-1-carbonyl)-8-methyl-1,2,3,4-tetrahydro-pyrido[4,3-b]indol-5-yl]-acetic acid | C27H26N2O4 442.513 | 1.07 (LC-4) | 443.14 |

TABLE 7-continued

| Ex. | Name | Mol Formula Mol Weight | $t_R$ [min] (Methode) | MS Data m/z [M + H]$^+$ |
|---|---|---|---|---|
| 90 | [2-(2-ethoxy-naphthalene-1-carbonyl)-7-methyl-1,2,3,4-tetrahydro-pyrido[4,3-b]indol-5-yl]-acetic acid | C27H26N2O4 442.513 | 1.07 (LC-4) | 443.14 |
| 91 | [2-(4-methoxy-naphthalene-1-carbonyl)-7-methyl-1,2,3,4-tetrahydro-pyrido[4,3-b]indol-5-yl]-acetic acid | C26H24N2O4 428.487 | 1.06 (LC-4) | 429.15 |
| 92 | [2-(2-fluoro-benzoyl)-1,2,3,4-tetrahydro-pyrido[4,3-b]indol-5-yl]-acetic acid | C20H17N2O3F 352.364 | 0.87 (LC-5) | 353.18 |
| 93 | [2-(3-fluoro-benzoyl)-1,2,3,4-tetrahydro-pyrido[4,3-b]indol-5-yl]-acetic acid | C20H17N2O3F 352.364 | 0.88 (LC-5) | 353.18 |
| 94 | [2-(3,5-difluoro-benzoyl)-1,2,3,4-tetrahydro-pyrido[4,3-b]indol-5-yl]-acetic acid | C20H16N2O3F2 370.354 | 0.90 (LC-5) | 371.17 |
| 95 | [2-(3,4,5-trifluoro-benzoyl)-1,2,3,4-tetrahydro-pyrido[4,3-b]indol-5-yl]-acetic acid | C20H15N2O3F3 388.344 | 0.92 (LC-5) | 389.14 |
| 96 | [2-(2,3,4,5-tetrafluoro-benzoyl)-1,2,3,4-tetrahydro-pyrido[4,3-b]indol-5-yl]-acetic acid | C20H14N2O3F4 406.334 | 0.94 (LC-5) | 407.13 |

Examples 97-106 of the following Table 8 are prepared using a procedure analogous to that described for Example 32, substituting the appropriate Intermediate for Intermediate 1 and the appropriate phenylhydrazine for 4-methoxyphenyl-hydrazine.

TABLE 8

| Ex. | Name | Mol Formula Mol Weight | $t_R$ [min] (Methode) | MS Data m/z [M + H]$^+$ |
|---|---|---|---|---|
| 97 | (2-benzoyl-8-fluoro-1,2,3,4-tetrahydro-pyrido[4,3-b]indol-5-yl)-acetic acid | C20H17N2O3F 352.364 | 1.99 (LC-6) | 353.13 |
| 98 | (2-benzoyl-6-chloro-1,2,3,4-tetrahydro-pyrido[4,3-b]indol-5-yl)-acetic acid | C20H17N2O3Cl 368.819 | 1.35 (LC-7) | 369.44 |
| 99 | (2-benzoyl-8-isopropyl-1,2,3,4-tetrahydro-pyrido[4,3-b]indol-5-yl)-acetic acid | C23H24N2O3 376.455 | 1.45 (LC-7) | 377.51 |
| 100 | (2-benzoyl-8-chloro-1,2,3,4-tetrahydro-pyrido[4,3-b]indol-5-yl)-acetic acid | C20H17N2O3Cl 368.819 | 1.35 (LC-7) | 369.44 |
| 101 | (2-benzoyl-7,8-dichloro-1,2,3,4-tetrahydro-pyrido[4,3-b]indol-5-yl)-acetic acid | C20H16N2O3Cl2 403.264 | 1.08 (LC-4) | 402.97[M − H]$^+$ |
| 102 | (2-benzoyl-8-trifluoromethyl-1,2,3,4-tetrahydro-pyrido[4,3-b]indol-5-yl)-acetic acid | C21H17N2O3F3 402.371 | 1.03 (LC-4) | 403.01 |
| 103 | (2-benzoyl-8-tert-butyl-1,2,3,4-tetrahydro-pyrido[4,3-b]indol-5-yl)-acetic acid | C24H26N2O3 390.481 | 1.07 (LC-4) | 389.17[M − H]$^+$ |
| 104 | (2-benzoyl-7-chloro-8-methyl-1,2,3,4-tetrahydro-pyrido[4,3-b]indol-5-yl)-acetic acid | C21H19N2O3Cl 382.846 | 1.04 (LC-4) | 381.14[M − H]$^+$ |
| 105 | (2-benzoyl-7,8-dimethyl-1,2,3,4-tetrahydro-pyrido[4,3-b]indol-5-yl)-acetic acid | C22H22N2O3 362.428 | 1.01 (LC-4) | 363.09 |
| 106 | (2-benzoyl-7-fluoro-1,2,3,4-tetrahydro-pyrido[4,3-b]indol-5-yl)-acetic acid | C20H17N2O3F 352.364 | 0.97 (LC-4) | 351.19[M − H]$^+$ |

Examples 107-149 of the following Table 9 are prepared using a procedure analogous to described for Example 53, substituting the appropriate acid for 2-ethoxynaphthoic acid.

TABLE 9

| Ex. | Name | Mol Formula Mol Weight | $t_R$ [min] (Methode) | MS Data m/z [M + H]$^+$ |
|---|---|---|---|---|
| 107 | [7-chloro-2-(2-naphthalen-1-yl-acetyl)-1,2,3,4-tetrahydro-pyrido[4,3-b]indol-5-yl]-acetic acid | C25H21N2O3Cl 432.906 | 1.13 (LC-4) | 433.03 |
| 108 | [8-chloro-2-(2-naphthalen-1-yl-acetyl)-1,2,3,4-tetrahydro-pyrido[4,3-b]indol-5-yl]-acetic acid | C25H21N2O3Cl 432.906 | 1.09 (LC-4) | 431.05[M − H]$^+$ |
| 109 | [7-methyl-2-(2-naphthalen-1-yl-acetyl)-1,2,3,4-tetrahydro-pyrido[4,3-b]indol-5-yl]-acetic acid | C26H24N2O3 412.488 | 1.11 (LC-4) | 413.09 |
| 110 | [8-bromo-2-(2-naphthalen-1-yl-acetyl)-1,2,3,4-tetrahydro-pyrido[4,3-b]indol-5-yl]-acetic acid | C25H21N2O3Br 477.357 | 1.16 (LC-4) | 477.01[M]$^+$ |
| 111 | [2-(4'-ethyl-biphenyl-4-carbonyl)-7-methyl-1,2,3,4-tetrahydro-pyrido[4,3-b]indol-5-yl]-acetic acid | C29H28N2O3 452.552 | 1.25 (LC-4) | 453.19 |
| 112 | [8-bromo-2-(4'-ethyl-biphenyl-4-carbonyl)-1,2,3,4-tetrahydro-pyrido[4,3-b]indol-5-yl]-acetic acid | C28H25N2O3Br 517.422 | 1.30 (LC-4) | 519.06 |

TABLE 9-continued

| Ex. | Name | Mol Formula Mol Weight | $t_R$ [min] (Methode) | MS Data m/z [M + H]+ |
|---|---|---|---|---|
| 113 | [2-(4'-ethyl-biphenyl-4-carbonyl)-8-fluoro-1,2,3,4-tetrahydro-pyrido[4,3-b]indol-5-yl]-acetic acid | C28H25N2O3F 456.516 | 1.22 (LC-4) | 457.14 |
| 114 | [6-chloro-2-(4'-ethyl-biphenyl-4-carbonyl)-1,2,3,4-tetrahydro-pyrido[4,3-b]indol-5-yl]-acetic acid | C28H25N2O3Cl 472.971 | 1.17 (LC-4) | 473.14 |
| 115 | [7-chloro-2-(4'-ethyl-biphenyl-4-carbonyl)-1,2,3,4-tetrahydro-pyrido[4,3-b]indol-5-yl]-acetic acid | C28H25N2O3Cl 472.971 | 1.27 (LC-4) | 473.14 |
| 116 | [8-chloro-2-(4'-ethyl-biphenyl-4-carbonyl)-1,2,3,4-tetrahydro-pyrido[4,3-b]indol-5-yl]-acetic acid | C28H25N2O3Cl 472.971 | 1.28 (LC-4) | 473.07 |
| 117 | [2-(4'-ethyl-biphenyl-4-carbonyl)-8-methyl-1,2,3,4-tetrahydro-pyrido[4,3-b]indol-5-yl]-acetic acid | C29H28N2O3 452.552 | 1.25 (LC-4) | 453.19 |
| 118 | [8-methyl-2-(2-naphthalen-1-yl-acetyl)-1,2,3,4-tetrahydro-pyrido[4,3-b]indol-5-yl]-acetic acid | C26H24N2O3 412.488 | 1.08 (LC-4) | 413.16 |
| 119 | [6-chloro-2-(2-naphthalen-1-yl-acetyl)-1,2,3,4-tetrahydro-pyrido[4,3-b]indol-5-yl]-acetic acid | C25H21N2O3Cl 432.906 | 1.12 (LC-4) | 433.03 |
| 120 | [8-chloro-2-(naphthalene-1-carbonyl)-1,2,3,4-tetrahydro-pyrido[4,3-b]indol-5-yl]-acetic acid | C24H19N2O3Cl 418.879 | 1.11 (LC-4) | 419.07 |
| 121 | [6-chloro-2-(naphthalene-1-carbonyl)-1,2,3,4-tetrahydro-pyrido[4,3-b]indol-5-yl]-acetic acid | C24H19N2O3Cl 418.879 | 1.09 (LC-4) | 419.04 |
| 122 | [7-methyl-2-(naphthalene-1-carbonyl)-1,2,3,4-tetrahydro-pyrido[4,3-b]indol-5-yl]-acetic acid | C25H22N2O3 398.461 | 0.95 (LC-5) | 399.25 |
| 123 | [8-methyl-2-(naphthalene-1-carbonyl)-1,2,3,4-tetrahydro-pyrido[4,3-b]indol-5-yl]-acetic acid | C25H22N2O3 398.461 | 0.95 (LC-5) | 399.22 |
| 124 | [8-bromo-2-(naphthalene-1-carbonyl)-1,2,3,4-tetrahydro-pyrido[4,3-b]indol-5-yl]-acetic acid | C24H19N2O3Br 463.33 | 1.12 (LC-4) | 464.96 |
| 125 | [8-fluoro-2-(naphthalene-1-carbonyl)-1,2,3,4-tetrahydro-pyrido[4,3-b]indol-5-yl]-acetic acid | C24H19N2O3F 402.424 | 1.08 (LC-4) | 403.01 |
| 126 | [8-fluoro-2-(2-naphthalen-1-yl-acetyl)-1,2,3,4-tetrahydro-pyrido[4,3-b]indol-5-yl]-acetic acid | C25H21N2O3F 416.451 | 1.06 (LC-4) | 415.05[M − H]+ |
| 127 | [2-(2-bromo-3-methyl-benzoyl)-7-chloro-1,2,3,4-tetrahydro-pyrido[4,3-b]indol-5-yl]-acetic acid | C21H18N2O3BrC 461.742 | 1.11 (LC-3) | 462.82 |
| 128 | [2-(2-bromo-3-methyl-benzoyl)-8-chloro-1,2,3,4-tetrahydro-pyrido[4,3-b]indol-5-yl]-acetic acid | C21H18N2O3BrCl 461.742 | 1.13 (LC-3) | 462.82 |
| 129 | [2-(2-bromo-3-methyl-benzoyl)-6-chloro-1,2,3,4-tetrahydro-pyrido[4,3-b]indol-5-yl]-acetic acid | C21H18N2O3BrCl 461.742 | 1.11 (LC-3) | 462.82 |
| 130 | [2-(2-bromo-3-methyl-benzoyl)-7-methyl-1,2,3,4-tetrahydro-pyrido[4,3-b]indol-5-yl]-acetic acid | C22H21N2O3Br 441.324 | 1.10 (LC-3) | 442.88 |
| 131 | [2-(2-bromo-3-methyl-benzoyl)-8-methyl-1,2,3,4-tetrahydro-pyrido[4,3-b]indol-5-yl]-acetic acid | C22H21N2O3Br 441.324 | 1.10 (LC-3) | 442.95 |
| 132 | [8-bromo-2-(2-bromo-3-methyl-benzoyl)-1,2,3,4-tetrahydro-pyrido[4,3-b]indol-5-yl]-acetic acid | C21H18N2O3Br2 506.193 | 1.15 (LC-3) | 506.85[M]+ |
| 133 | [2-(2-bromo-3-methyl-benzoyl)-8-fluoro-1,2,3,4-tetrahydro-pyrido[4,3-b]indol-5-yl]-acetic acid | C21H18N2O3BrF 445.287 | 1.05 (LC-3) | 446.89 |
| 134 | [8-bromo-2-(2-ethoxy-naphthalene-1-carbonyl)-1,2,3,4-tetrahydro-pyrido[4,3-b]indol-5-yl]-acetic acid | C26H23N2O4Br 507.383 | 1.12 (LC-4) | 508.79 |
| 135 | [2-(2-ethoxy-naphthalene-1-carbonyl)-8-fluoro-1,2,3,4-tetrahydro-pyrido[4,3-b]indol-5-yl]-acetic acid | C26H23N2O4F 446.477 | 1.06 (LC-4) | 446.97 |
| 136 | [8-chloro-2-(2-ethoxy-naphthalene-1-carbonyl)-1,2,3,4-tetrahydro-pyrido[4,3-b]indol-5-yl]-acetic acid | C26H23N2O4Cl 462.932 | 1.09 (LC-4) | 463.4 |
| 137 | [2-(4-methoxy-naphthalene-1-carbonyl)-1,2,3,4-tetrahydro-pyrido[4,3-b]indol-5-yl]-acetic acid | C25H22N2O4 414.46 | 1.04 (LC-4) | 413.19[M − H]+ |
| 138 | [2-(5-bromo-naphthalene-1-carbonyl)-1,2,3,4-tetrahydro-pyrido[4,3-b]indol-5-yl]-acetic acid | C24H19N2O3Br 463.33 | 1.06 (LC-4) | 464.82 |
| 139 | [2-(4-methyl-naphthalene-1-carbonyl)-1,2,3,4-tetrahydro-pyrido[4,3-b]indol-5-yl]-acetic acid | C25H22N2O3 398.461 | 1.04 (LC-4) | 397.13[M − H]+ |
| 140 | [2-(2-methyl-naphthalene-1-carbonyl)-1,2,3,4-tetrahydro-pyrido[4,3-b]indol-5-yl]-acetic acid | C25H22N2O3 398.461 | 1.03 (LC-4) | 397.20[M − H]+ |
| 141 | [2-(biphenyl-3-carbonyl)-1,2,3,4-tetrahydro-pyrido[4,3-b]indol-5-yl]-acetic acid | C26H22N2O3 410.472 | 1.07 (LC-4) | 409.17[M − H]+ |
| 142 | [2-(4-fluoro-naphthalene-1-carbonyl)-1,2,3,4-tetrahydro-pyrido[4,3-b]indol-5-yl]-acetic acid | C24H19N2O3F 402.424 | 1.04 (LC-4) | 401.14[M − H]+ |
| 143 | [2-(2-methoxy-naphthalene-1-carbonyl)-1,2,3,4-tetrahydro-pyrido[4,3-b]indol-5-yl]-acetic acid | C25H22N2O4 414.46 | 1.01 (LC-4) | 413.19[M − H]+ |
| 144 | [2-(9-oxo-9H-fluorene-2-carbonyl)-1,2,3,4-tetrahydro-pyrido[4,3-b]indol-5-yl]-acetic acid | C27H20N2O4 436.466 | 1.04 (LC-4) | 435.20[M − H]+ |
| 145 | [2-(9H-fluorene-1-carbonyl)-1,2,3,4-tetrahydro-pyrido[4,3-b]indol-5-yl]-acetic acid | C27H22N2O3 422.483 | 1.07 (LC-4) | 423.01 |
| 146 | [2-(9H-fluorene-4-carbonyl)-1,2,3,4-tetrahydro-pyrido[4,3-b]indol-5-yl]-acetic acid | C27H22N2O3 422.483 | 1.05 (LC-4) | 421.21[M − H]+ |
| 147 | [2-(2,4,6-trifluoro-benzoyl)-1,2,3,4-tetrahydro-pyrido[4,3-b]indol-5-yl]-acetic acid | C20H15N2O3F3 388.344 | 0.90 (LC-5) | 389.1 |
| 148 | [2-(4-cyclohexyl-benzoyl)-1,2,3,4-tetrahydro-pyrido[4,3-b]indol-5-yl]-acetic acid | C26H28N2O3 416.519 | 1.03 (LC-5) | 417.22 |

TABLE 9-continued

| Ex. | Name | Mol Formula Mol Weight | $t_R$ [min] (Methode) | MS Data m/z [M + H]$^+$ |
|---|---|---|---|---|
| 149 | [2-(1H-indole-4-carbonyl)-1,2,3,4-tetrahydro-pyrido[4,3-b]indol-5-yl]-acetic acid | C22H19N3O3 373.411 | 0.84 (LC-5) | 374.19 |

Examples 150-171 of the following Table 10 are prepared using a procedure analogous to described for Example 57, substituting the appropriate isocyanate or isothiocyanate, respectively, for phenyl isocyanate.

TABLE 10

| Ex. | Name | Mol Formula Mol Weight | $t_R$ [min] (Methode) | MS Data m/z [M + H]$^+$ |
|---|---|---|---|---|
| 150 | [2-(2-fluoro-phenylcarbamoyl)-1,2,3,4-tetrahydro-pyrido[4,3-b]indol-5-yl]-acetic acid | C20H18N3O3F 367.379 | 0.99 (LC-3) | 368.00 |
| 151 | [2-(3-fluoro-phenylcarbamoyl)-1,2,3,4-tetrahydro-pyrido[4,3-b]indol-5-yl]-acetic acid | C20H18N3O3F 367.379 | 1.02 (LC-3) | 368.00 |
| 152 | [2-(4-fluoro-phenylcarbamoyl)-1,2,3,4-tetrahydro-pyrido[4,3-b]indol-5-yl]-acetic acid | C20H18N3O3F 367.379 | 1.00 (LC-3) | 368.07 |
| 153 | (2-o-tolylcarbamoyl-1,2,3,4-tetrahydro-pyrido[4,3-b]indol-5-yl)-acetic acid | C21H21N3O3 363.416 | 0.99 (LC-3) | 364.03 |
| 154 | (2-m-tolylcarbamoyl-1,2,3,4-tetrahydro-pyrido[4,3-b]indol-5-yl)-acetic acid | C21H21N3O3 363.416 | 1.03 (LC-3) | 364.06 |
| 155 | (2-p-tolylcarbamoyl-1,2,3,4-tetrahydro-pyrido[4,3-b]indol-5-yl)-acetic acid | C21H21N3O3 363.416 | 1.02 (LC-3) | 363.57 |
| 156 | (2-benzylcarbamoyl-1,2,3,4-tetrahydro-pyrido[4,3-b]indol-5-yl)-acetic acid | C21H21N3O3 363.416 | 0.98 (LC-3) | 364.47 |
| 157 | (2-phenethylcarbamoyl-1,2,3,4-tetrahydro-pyrido[4,3-b]indol-5-yl)-acetic acid | C22H23N3O3 377.443 | 1.00 (LC-3) | 378.04 |
| 158 | [2-(naphthalen-1-ylcarbamoyl)-1,2,3,4-tetrahydro-pyrido[4,3-b]indol-5-yl]-acetic acid | C24H21N3O3 399.449 | 1.03 (LC-3) | 399.97 |
| 159 | [2-(naphthalen-2-ylcarbamoyl)-1,2,3,4-tetrahydro-pyrido[4,3-b]indol-5-yl]-acetic acid | C24H21N3O3 399.449 | 1.08 (LC-3) | 400.14 |
| 160 | [2-(biphenyl-2-ylcarbamoyl)-1,2,3,4-tetrahydro-pyrido[4,3-b]indol-5-yl]-acetic acid | C26H23N3O3 425.487 | 1.09 (LC-3) | 426.18 |
| 161 | (2-cyclohexylcarbamoyl-1,2,3,4-tetrahydro-pyrido[4,3-b]indol-5-yl)-acetic acid | C20H25N3O3 355.437 | 1.01 (LC-3) | 356.16 |
| 162 | [2-(2-chloro-phenylcarbamoyl)-1,2,3,4-tetrahydro-pyrido[4,3-b]indol-5-yl]-acetic acid | C20H18N3O3Cl 383.834 | 1.03 (LC-3) | 383.96 |
| 163 | [2-(4-fluoro-phenylthiocarbamoyl)-1,2,3,4-tetrahydro-pyrido[4,3-b]indol-5-yl]-acetic acid | C20H18N3O2FS 383.446 | 1.02 (LC-4) | 383.91[M]$^+$ |
| 164 | (2-phenylthiocarbamoyl-1,2,3,4-tetrahydro-pyrido[4,3-b]indol-5-yl)-acetic acid | C20H19N3O2S 365.456 | 1.01 (LC-4) | 364.12[M − H]$^+$ |
| 165 | (2-phenethylthiocarbamoyl-1,2,3,4-tetrahydro-pyrido[4,3-b]indoL-5-yl)-acetic acid | C22H23N3O2S 393.51 | 1.07 (LC-4) | 392.08[M − H]$^+$ |
| 166 | (2-cyclohexylthiocarbamoyl-1,2,3,4-tetrahydro-pyrido[4,3-b]indol-5-yl)-acetic acid | C20H25N3O2S 371.504 | 1.07 (LC-4) | 372.01 |
| 167 | (2-benzylthiocarbamoyl-1,2,3,4-tetrahydro-pyrido[4,3-b]indol-5-yl)-acetic acid | C21H21N3O2S 379.483 | 1.05 (LC-4) | 378.10[M − H]$^+$ |
| 168 | [2-(2-chloro-phenylthiocarbamoyl)-1,2,3,4-tetrahydro-pyrido[4,3-b]indol-5-yl]-acetic acid | C20H18N3O2ClS 399.901 | 1.03 (LC-4) | 398.10[M − H]$^+$ |
| 169 | (2-p-tolylthiocarbamoyl-1,2,3,4-tetrahydro-pyrido[4,3-b]indol-5-yl)-acetic acid | C21H21N3O2S 379.483 | 1.05 (LC-4) | 378.10[M − H]$^+$ |
| 170 | (2-m-tolylthiocarbamoyl-1,2,3,4-tetrahydro-pyrido[4,3-b]indol-5-yl)-acetic acid | C21H21N3O2S 379.483 | 1.07 (LC-4) | 380.05 |
| 171 | (2-o-tolylthiocarbamoyl-1,2,3,4-tetrahydro-pyrido[4,3-b]indol-5-yl)-acetic acid | C21H21N3O2S 379.483 | 1.05 (LC-4) | 378.10[M − H]$^+$ |

TABLE 11

NMR data of Intermediates 1-8 are given below.

Chemical shifts(δ) in parts per million(ppm), solvent DMSO-d$_6$

| | |
|---|---|
| Intermediate 1 | 1.20(t, J=7.0Hz, 3H); 2.97(t, J=5.8Hz, 2H); 3.45(t, J=5.8Hz, 2H); 4.13(q, J=7.0Hz, 2H); 4.30(s, 2H); 5.08(s, 2H); 7.05(t, J=7.6Hz, 1H); 7.14(t, J=7.6Hz, 1H); 7.41(d, J=8.2Hz); 7.48(d, J=7.6Hz, 1H); 9.55(br s, 2H). |
| Intermediate 2 | 1.20(t, J=7.0Hz, 3H); 2.97(ps t, J=5.8, 5.3Hz, 2H); 3.43(ps t, J=5.3, 4.7Hz, 2H); 4.13(q, J=7.0Hz, 2H); 4.28(br s, 2H); 5.10(s, 2H); 7.25(dd, J=8.8, 1.8Hz, 1H); 7.42(d, J=8.8Hz, 1H); 7.73(d, J=1.8Hz, 1H); 9.61(br s, 2H). |

TABLE 11-continued

NMR data of Intermediates 1-8 are given below.

Chemical shifts(δ) in parts per million(ppm), solvent DMSO-$d_6$

| | |
|---|---|
| Intermediate 3 | 1.20(t, J=7.0Hz, 3H); 2.36(s, 3H); 2.94(t, J=5.8Hz, 2H); 3.44(m, 2H); 4.12(q, J=7.0Hz, 2H); 4.27(br s, 2H); 5.03(s, 2H); 7.00(dd, J=8.8, 1.8Hz, 1H); 7.25-7.30(m, 2H); 9.45(br s, 2H). |
| Intermediate 4 | 1.21(t, J=7.0Hz, 3H); 2.38(s, 3H); 2.94(m, 2H); 3.43(m, 2H); 4.13(q, J=7.0Hz, 2H); 4.27(br s, 2H); 5.02(s, 2H); 6.88(d, J=8.2Hz, 1H); 7.20(s, 1H); 7.35(d, J=8.2Hz, 1H); 9.50(br s, 2H). |
| Intermediate 5 | 1.21(t, J=7.0Hz, 3H); 2.95(t, J=5.8Hz, 2H); 3.44(m, 2H); 4.14(q, J=7.0Hz, 2H); 4.29(s, 2H); 5.12(s, 2H); 7.08(dd, J=8.2, 1.8Hz, 1H); 7.50(d, J=8.2Hz, 1H); 7.62(d, J=1.8Hz, 1H); 9.52(br s, 2H). |
| Intermediate 6 | 1.20(t, J=7.0Hz, 3H); 2.96(t, J=5.8Hz, 2H); 3.45(t, J=5.8Hz, 2H); 4.13(q, J=7.0Hz, 2H); 4.29(s, 2H); 5.11(s, 2H); 7.14(dd, J=8.8, 1.8Hz, 1H); 7.47(d, J=8.8Hz, 1H); 7.60(d, J=2.3Hz, 1H); 9.41(br s, 2H). |
| Intermediate 7 | 1.20(t, J=7.0Hz, 3H); 2.98(t, J=5.8Hz, 2H); 3.46(m, 2H); 4.16(q, J=7.0Hz, 2H); 4.29(br s, 2H); 5.26(s, 2H); 7.05(t, J=7.6Hz, 1H); 7.15(dd, J=7.6, 1.2Hz, 1H); 7.48(dd, J=7.6, 1.2Hz, 1H); 9.62(br s, 2H). |
| Intermediate 8 | 1.20(t, J=7.0Hz, 3H); 2.96(ps t, J=5.8, 5.3Hz, 2H); 3.44(m, 2H); 4.13(q, J=7.0Hz, 2H); 4.26(br s, 2H); 5.09(s, 2H); 6.97(td, J=9.4, 2.3Hz, 1H); 7.32(dd, J=10.0, 2.3Hz, 1H); 7.41-7.46(m, 1H); 9.62(br s, 2H). |

TABLE 12

NMR data of selected Examples are given below.

| Example No. | Chemical shifts(δ) in parts per million(ppm), solvent: DMSO-$d_6$ |
|---|---|
| 1 | 1.43(s, 9H); 2.70(ps t, J=5.8, 5.3Hz, 2H); 3.70(ps t, J=5.8, 5.3Hz, 2H); 4.53(s, 2H); 4.89(s, 2H); 7.00(t, J=7.6Hz, 1H); 7.07(td, J=8.2, 1.2Hz, 1H); 7.35(d, J=8.2Hz, 1H); 7.40(d, J=7.6Hz, 1H). |
| 8 | mixture of rotamers: 2.79(m, 2H); 3.65/3.99(m, 2H); 4.59/4.79(m, 2H); 4.91(s, 2H); 6.94-7.18(m, 2H); 7.37(d, J=7.6Hz, 1H); 7.42-7.49(m, 6H); 13.0(br s, 1H). |
| 12 | mixture of rotamers: 2.84(m, 2H); 3.96(ps t, J=5.3, 5.9Hz, 2H); 4.83(br s, 2H); 4.90(s, 2H); 6.99(ps t, J=7.6, 7.0Hz, 1H); 7.07(ps t, J=7.6, 7.0Hz, 1H); 7.13-7.16(m, 1H); 7.36(d, J=7.6Hz, 1H); 7.42(d, J=7.6Hz, 1H); 7.53(d, J=2.9Hz, 1H); 7.76(d, J=4.7Hz, 1H); 13.0(br s, 1H). |
| 39 | mixture of rotamers/atropisomers: 2.33/2.36(s, 3H); 2.58-2.79(m 2H); 3.46/3.99(t, J=5.3Hz, 2H); 2.30-4.92(m, 2H); 4.82/4.87(s, 2H); 6.84-7.17(m, 3H); 7.26-7.39(m, 3H); 7.46(d, J=7.6Hz, 1H); 12.9(br s, 1H). |
| 51 | mixture of rotamers/atropisomers: 2.71-2.78(m, 2H); 3.87-3.96(m, 2H); 4.31(s, 2H); 4.69(s, 1H); 4.88-4.92(m, 3H); 6.97-7.11(m, 2H); 7.33-7.51(m, 6H); 7.76-7.82(m, 1H); 7.88-7.98(m, 2H); 13.0(br s, 1H). |
| 57 | 2.77(m, 2H); 3.83(t, J=5.3Hz, 2H); 4.67(s, 2H); 4.91(s, 2H); 6.91(t, J=7.0Hz, 1H); 6.99-7.10(m, 2H); 7.19-7.24(m, 2H); 7.35-7.47(m, 4H); 8.64(s, 1H); 13.0(br s, 1H). |
| 61 | mixture of rotamers: 1.41(s, 9H); 2.64-2.70(m, 2H); 3.66-3.69(m, 2H); 4.51/4.79(br s, 2H); 4.91(s, 2H); 7.00(d, J=8.8Hz, 1H); 7.36(d, J=8.8Hz, 1H); 7.54(s, 1H); 12.9(br s, 1H). |
| 63 | 1.42(s, 9H); 2.69(t, J=5.3Hz, 2H); 3.70(t, J=5.3Hz, 2H); 4.51(s, 2H); 5.13(s, 2H); 6.99(t, J=7.6Hz, 1H); 7.09(d, J=7.0Hz, 1H); 7.41(d, J=7.6Hz, 1H); 13.0(br s, 1H). |
| 64 | 1.42(s, 9H); 2.38(s, 3H); 2.67(t, J=5.3Hz, 2H); 3.69(t, J=5.3Hz, 2H); 4.49(s, 2H); 4.84(s, 2H); 6.84(d, J=7.6Hz, 1H); 7.15(s, 1H); 7.28(d, J=7.6Hz, 1H); 12.9(br s, 1H). |
| 65 | 1.42(s, 9H); 2.67(t, J=5.3Hz, 2H); 3.69(t, J=5.3Hz, 2H); 4.49(s, 2H); 4.85(s, 2H); 6.90(d, J=8.2Hz, 1H); 7.18(s, 1H); 7.23(d, J=8.2Hz, 1H); 12.9(br s, 1H). |
| 67 | 1.42(s, 9H); 2.68(m, 2H); 3.68(m, 2H); 4.49(m, 2H); 4.90(s, 2H); 6.90(td, J=9.3, 2.1Hz, 1H); 7.22(dd, J=9.3, 2.1Hz, 1H); 7.38(dd, J=8.8, 3.9Hz, 1H); 13.0(br s, 1H). |
| 68 | mixture of rotamers: 2.79(m, 2H); 3.64/4.01(m, 2H); 4.56/4.78(m, 2H); 5.13(s, 2H); 6.92-7.11(m, 2H); 7.28-7.57(m, 5H); 13.1(br s, 1H). |
| 73 | mixture of rotamers (ratio 1.5:1): 2.79(m, 2H); 3.63/3.98 m, 2H); 4.56/4.77(m, 2H); 4.93(s, 2H); 7.16-7.22(m, 2H); 7.36-7.41(m, 2H); 7.46-7.73(m, 4H); 13.1(br s, 1H). |
| 74 | 2.78(br s, 2H); 3.63 and 3.99(m, 2H); 4.54 and 4.76(m, 2H); 4.92(s, 2H); 6.92(m, 1H); 7.36(m, 3H); 7.51(m, 3H); 13.02(s, 1H). |

TABLE 12-continued

NMR data of selected Examples are given below.

| Example No. | Chemical shifts(δ) in parts per million(ppm), solvent: DMSO-d$_6$ |
|---|---|
| 75 | mixture of rotamers: 2.83(m, 2H); 3.95(t, J=5.3Hz, 2H); 4.82(br s, 2H); 4.93(s, 2H); 7.07(dd, J=8.8, 1.7Hz, 1H); 7.15(t, J=5.3Hz, 1H); 7.41(d, J=8.8Hz, 1H); 7.53-7.55(m, 2H); 7.77(d, J=5.3Hz, 1H); 13.0(br s, 1H). |
| 77 | mixture of rotamers: 2.84(m, 2H); 3.96(t, J=5.3Hz, 2H); 4.84(br s, 2H); 4.94(s, 2H); 7.16(t, J=4.7Hz, 1H); 7.19(d, J=8.8Hz, 1H); 7.38(d, J=8.8Hz, 1H); 7.55(d, J=2.3Hz, 1H); 7.70(s, 1H); 7.78(d, J=4.7Hz, 1H); 13.0(br s, 1H). |
| 78 | 2.84(m, 2H); 3.97(pst, J=5.8, 5.3Hz, 2H); 4.81(br s, 2H); 4.93(s, 2H); 6.91(td, J=8.8, 2.3Hz, 1H); 7.16(t, J=4.1Hz, 1H); 7.28(dd, J=9.9, 1.8Hz, 1H); 7.37-7.42(m, 1H); 7.53(d, J=2.9Hz, 1H); 7.78(d, J=4.7Hz, 1H); 13.0(br s, 1H). |
| 79 | mixture of rotamers: 2.84(m, 2H); 3.96(t, J=5.3Hz, 2H); 4.83/5.11(br s, 2H); 4.95(s, 2H); 7.01(dd, J=8.2, 1.7Hz, 1H); 7.14 td, J=5.3, 1.7Hz, 1H); 7.37-7.54(m, 2H); 7.56(d, J=1.7Hz, 1H); 7.78(d, J=5.3Hz, 1H); 13.0(br s, 1H). |
| 82 | mixture of rotamers/atropisomers: 2.51-2.89(m, 2H); 3.47/3.96(m, 2H); 3.73/3.89(s, 3H); 4.18-4.38(m, 1H); 4.87-5.01(m, 3H); 6.79-6.98(m, 1H); 7.31-7.54(m, 6H); 7.87-7.94(m, 1H); 7.99-8.04(m, 1H); 13.0(br s, 1H). |
| 107 | 2.65-7.72(m, 2H); 3.81-3.90(m, 2H); 4.25(s, 2H); 4.63/4.83(s, 2H); 4.89(s, 2H); 6.94-7.00(m, 1H); 7.27-7.46(m, 5H); 7.52(d, J=2.9Hz, 1H); 7.74(t, J=8.8Hz, 1H); 7.83-7.94(m, 2H); 13.0(s br, 1H). |
| 108 | mixture of rotamers and atropisomers: 2.51-2.89(m, 2H); 3.30/3.47(m, 2H); 3.73/3.89(s, 3H); 4.18-4.38(m, 1H); 4.87-5.01(m, 3H); 6.79-6.98(m, 1H); 7.31-7.54(m, 6H); 7.87-7.94(m, 1H); 7.99-8.04(m, 1H); 13.0(br s, 1H). |
| 109 | mixture of isomers: 2.36/2.51(s, 3H); 2.69-2.74(m, 2H); 3.81-3.92(m, 2H); 4.28(s, 2H); 4.65(s, 1H); 4.83-5.00(m, 3H); 6.82(d, J=8.2Hz, 1H); 7.13-7.16(m, 1H); 7.28-7.50(m, 5H); 7.78(t, J=8.2Hz, 1H); 7.87-7.98(m, 2H); 12.9(br s, 1H). |
| 110 | mixture of rotamers: 2.71-2.79(m, 2H); 3.86-3.95(m, 2H); 4.28/4.30(s, 2H); 4.67/4.88(s, 2H); 4.93/4.95(s, 2H); 7.20(d, J=8.0Hz, 1H); 7.33-7.52(m, 5H); 7.66(s, 1H); 7.80(t, J=8.0Hz, 1H); 7.88-7.98(m, 2H); 13.0(br s, 1H). |
| 111 | mixture of rotamers: 1.19(t, J=7.6Hz, 3H); 3.36(s, 3H); 2.63(q, J=7.6Hz, 2H); 2.78(m, 2H); 3.71/3.98(m, 2H); 4.63-4.75/5.03(m, 2H); 4.85/4.86(s, 2H); 6.75-6.93/7.36(m, 2H); 7.15(s, 1H); 7.30(d, J=8.2Hz, 2H); 7.50(d, J=8.2Hz, 2H); 7.61(d, J=8.2Hz, 2H); 7.72(d, J=8.2Hz, 2H); 13.0(br s, 1H). |
| 112 | mixture of rotamers: 1.20(t, J=7.6Hz, 3H); 2.64(q, J=7.6Hz, 2H); 2.81(m, 2H); 3.72/3.99(m, 2H); 4.66-4.81(m, 2H); 4.94(s, 2H); 7.20(br s, 1H); 7.32(d, J=8.2Hz, 2H); 7.38(d, J=8.2Hz, 1H); 7.52(d, J=8.2Hz, 2H); 7.63(d, J=8.2Hz, 2H); 7.73(d, J=8.2Hz, 3H); 13.1(br s, 1H). |
| 113 | mixture of rotamers: 1.18(t, J=7.6Hz, 3H); 2.62(q, J=7.6Hz, 2H); 2.79(m, 2H); 3.71-3.97(m, 2H); 4.62-4.74(m, 2H); 4.91(s, 2H); 6.86-7.14(m, 2H); 7.30(d, J=8.2Hz, 2H); 7.35-7.39(m, 1H); 7.50(d, J=8.2Hz, 2H); 7.61(d, J=8.2Hz, 2H); 7.71(d, J=8.2Hz, 2H); 13.0(br s, 1H). |
| 114 | mixture of rotamers: 1.19(t, J=7.6Hz, 3H); 2.63(q, J=7.6Hz, 2H); 2.82(m, 2H); 3.69-4.03(m, 2H); 4.64-4.81(m, 2H); 5.14(s, 2H); 6.96-7.14(m, 2H); 7.31(d, J=8.2Hz, 3H); 7.52(d, J=8.2Hz, 2H); 7.62(d, J=8.2Hz, 2H); 7.72(d, J=8.2Hz, 2H); 13.1(br s, 1H). |
| 115 | mixture of rotamers: 1.20(t, J=7.6Hz, 3H); 2.64(q, J=7.6Hz, 2H); 2.30(m, 2H); 3.71-3.99(m, 2H); 4.66-4.79/5.00-5.08(m, 2H); 4.96(s, 2H); 6.91-7.08(m, 1H); 7.32(d, J=8.2Hz, 2H); 7.53-7.41(m, 1H); 7.52(d, J=8.2Hz, 2H); 7.56(s, 1H); 7.63(d, J=8.2Hz, 2H); 7.73(d, J=8.8Hz, 2H); 13.0(br s, 1H). |
| 116 | mixture of rotamers: 1.20(t, J=7.6Hz, 3H); 2.64(q, J=7.6Hz, 2H); 2.81(m, 2H); 3.73/4.00(m, 2H); 4.67-4.78(m, 2H); 4.94(s, 2H); 7.08(m, 1H); 7.32(d, J=8.2Hz, 2H); 7.42(d, J=8.8Hz, 1H); 7.52(d, J=8.2Hz, 2H); 7.63(d, J=8.2Hz, 2H); 7.73(d, J=8.2Hz, 2H); 13.0(br s, 1H). |
| 117 | mixture of rotamers: 1.20(t, J=7.6Hz, 3H); 2.37(s, 3H); 2.64(q, J=7.6Hz, 2H); 2.79(m, 2H); 3.72/4.00(m, 2H); 4.64-4.77(m, 2H); 4.86(s, 2H); 6.90(m, 1H); 7.03-7.16(m, 1H); 7.24(d, J=8.2Hz, 1H); 7.32(d, J=8.2Hz, 2H); 7.52(d, J=8.2Hz, 2H); 7.63(d, J=8.2Hz, 2H); 7.73(d, J=8.2Hz, 2H); 13.0(br s, 1H). |
| 119 | mixture of rotamers: 2.71-2.81(m, 2H); 3.87-3.96(m, 2H); 4.29/4.31(s, 2H); 4.68/4.87(br s, 2H); 5.13/5.15(s, 2H); 6.98/6.99(t, J=7.6Hz, 1H); 7.09/7.10(d, J=7.6Hz, 1H); 7.32-7.52(m, 5H); 7.79(t, J=8.8Hz, 1H); 7.88-7.98(m, 2H); 13.1(br s, 1H). |
| 120 | mixture of rotamers/atropisomers: 2.51-2.90(m, 2H); 3.22-3.47(m, 2H); 4.01-4.35(m, 1H); 4.87-5.02(m, 3H); 6.96-7.13(m, 1H); 7.34-7.72(m, 7H); 7.94-8.00(m, 2H); 13.0(br s, 1H). |

TABLE 12-continued

NMR data of selected Examples are given below.

| Example No. | Chemical shifts(δ) in parts per million(ppm), solvent: DMSO-$d_6$ |
|---|---|
| 121 | mixture of rotamers: 2.41-2.93(m, 2H); 3.30/3.49(m, 2H); 4.01-4.37/4.89-5.00(m, 2H); 5.09/5.18(s, 2H); 6.76/6.82/6.98-7.03(m, 1H); 7.06/7.14(d, J=7.6Hz, 1H); 7.41-7.60(m, 5H); 7.68/7.73(d, J=8.2Hz, 1H); 7.97-8.02(d, J=7.6Hz, 2H); 13.1(br s, 1H). |
| 124 | mixture of rotamers/atropisomers: 2.53-2.90(m, 2H); 3.23-3.47(m, 2H); 4.01-4.36(m, 1H); 4.87-5.02(m, 3H); 7.10/7.21(dd, J=8.9, 1.2Hz, 1H); 7.28-7.77(m, 7H); 7.95-8.01(m, 2H); 13.0(br s, 1H). |
| 128 | mixture of rotamers and atropisomers: 2.36/2.40(s, 3H); 2.65-2.84(m, 2H); 3.49/4.01(t, J=5.9Hz, 2H); 4.33/4.74(s, 2H); 4.90/4.94(s, 2H); 7.02-7.18(m, 2H); 7.30-7.41(m, 3H); 7.44/7.60(s, 1H); 13.0(br s, 1H). |
| 129 | mixture of rotamers and atropisomers: 2.35/2.40(s, 3H); 2.67-2.74/2.81-2.86(m, 2H); 3.49-3.52/3.95-4.10(m, 2H); 4.32/4.70/4.76/4.89/4.94(s, 2H); 5.11/5.16(s, 2H); 6.86-7.21(m, 3H); 7.30-7.52(m, 3H); 13.0(br s, 1H). |
| 130 | mixture of rotamers and atropisomers: 2.31/2.33(s, 3H); 2.36/2.37(s, 3H); 2.60-2.79(m, 2H); 3.46/3.99(t, J=5.3Hz, 2H); 4.28-4.90(m, 2H); 4.79/4.84(s, 2H); 6.71/6.85(d, J=8.2Hz, 1H); 7.03-7.40(m, 5H); 12.9(br s, 1H). |
| 131 | mixture of rotamers and atropisomers: 2.26/2.40(s, 3H); 2.37(s, 3H); 2.59-2.81(m, 2H); 3.49/4.02(m, 2H); 4.30/4.72(s, 2H); 4.83/4.87(s, 2H); 6.85-6.97(m, 1H); 7.08-7.42(m, 5H); 12.9(br s, 1H). |
| 132 | mixture of rotamers and atropisomers: 2.36/2.40(s, 3H); 2.63-2.84(m, 2H); 3.49/4.01(t, J=5.3Hz, 2H); 4.33/4.74(s, 2H); 4.90/4.94(s, 2H); 7.02-7.23(m, 2H); 7.30-7.42(m, 3H); 7.47/7.74(d, J=1.8Hz, 1H); 13.0(br s, 1H). |
| 133 | mixture of rotamers and atropisomers: 2.33/2.37(s, 3H); 2.59-2.81(m, 2H); 3.45-3.49/3.97-4.02(m, 2H); 4.28-4.84(m, 2H); 4.87/4.91(s, 2H); 6.81-6.94(m, 1H); 7.03-7.40(m, 5H); 13.0(br s, 1H). |
| 150 | 2.77(t, J=5.3Hz, 2H); 3.83(t, J=5.3Hz, 2H); 4.67(s, 2H); 4.92(s, 2H); 6.69-7.21(m, 5H); 7.36-7.45(m, 3H); 8.44(s, 1H); 13.0(br s, 1H). |
| 151 | 2.77(t, J=5.3Hz, 2H); 3.83(t, J=5.3Hz, 2H); 4.67(s, 2H); 4.92(s, 2H); 6.69(m, 1H); 7.02(t, J=7.6Hz, 1H); 7.09(t, J=8.2Hz, 1H); 7.24(d, J=8.2Hz, 1H); 7.27(s, 1H); 7.37(d, J=7.6Hz, 1H); 7.41-7.47(m, 2H); 8.86(s, 1H); 13.0(br s, 1H). |
| 152 | 2.76(t, J=4.7Hz, 2H); 3.83(t, J=5.3Hz, 2H); 4.66(s, 2H); 4.92(s, 2H); 6.99-7.11(m, 4H); 7.36-7.49(m, 4H); 8.69(s, 1H); 13.0(br s, 1H). |
| 153 | 2.15(s, 3H); 2.74-2.81(m, 2H); 3.83(t, J=5.3Hz, 2H); 4.66(s, 2H); 4.92(s, 2H); 6.99-7.19(m, 6H); 7.36-7.42(m, 2H); 8.18(s, 1H); 13.0(br s, 1H). |
| 154 | 2.18(s, 3H); 2.71(t, J=4.7Hz, 2H); 3.77(t, J=5.3Hz, 2H); 4.61(s, 2H); 4.87(s, 2H); 6.69(d, J=7.6Hz, 1H); 6.95-7.07(m, 3H); 7.22(d, J=8.8Hz, 1H); 7.24(s, 1H); 7.32(d, J=7.6Hz, 1H); 7.37(d, J=7.6Hz, 1H); 8.52(s, 1H); 12.9(br s, 1H). |
| 155 | 2.21(s, 3H); 2.76(t, J=5.3Hz, 2H); 3.82(t, J=5.3Hz, 2H); 4.65(s, 2H); 4.91(s, 2H); 6.99-7.11(m, 4H); 7.33-7.43(m, 4H); 8.55(s, 1H); 13.0(br s, 1H). |
| 156 | 2.70(t, J=5.3Hz, 2H); 3.74(t, J=5.3Hz, 2H); 4.28(d, J=5.3Hz, 2H); 4.56(s, 2H); 4.90(s, 2H); 7.01(t, J=7.6Hz, 1H); 7.08(t, J=7.6Hz, 1H); 7.16-7.31(m, 6H); 7.36(d, J=7.6Hz, 1H); 7.38(d, J=7.6Hz, 1H); 13.0(br s, 1H). |
| 159 | 2.75(m, 2H); 3.83(t, J=5.3Hz, 2H); 4.68(s, 2H); 4.88(s, 2H); 6.96-7.07(m, 2H); 7.25-7.40(m, 4H); 7.59(dd, J=8.8, 1.8Hz, 1H); 7.68(d, J=8.2Hz, 1H); 7.73(d, J=8.8Hz, 2H); 7.97(d, J=1.8Hz, 1H); 8.84(s, 1H); 12.9(br s, 1H). |
| 162 | 2.78(m, 2H); 3.84(t, J=5.3Hz, 2H); 4.68(s, 2H); 4.92(s, 2H); 6.99-7.16(m, 3H); 7.27(t, J=7.6Hz, 1H); 7.36=7.49(m, 4H); 8.34(s, 1H); 13.0(br s, 1H). |

Biological Assay:

Preparation of CRTH2 Membranes and Radioligand Binding Assay:

Preparation of the membranes and radioligand binding assays are performed according to known procedures, e.g. Sawyer N. et al. (*Br. J. Pharmacol.*, 2002, 137, 1163-1172). A clonal HEK 293 cell line, expressing high level of recombinant hCRTH2 receptor, is selected for the preparation of membranes. Cells are detached from culture plates in 5 ml buffer A per plate (5 mM Tris, 1 mM $MgCl_2$x6 $H_2O$, 0.1 mM PMSF, 0.1 mM phenanthroline) using a police rubber and transferred into centrifugation tubes and frozen at −80° C. After thawing, the cells are centrifuged at 500 g for 5 min and then resuspended in buffer A. Cells are then fragmented by homogeinization with a Polytron homogenizer for 30 s. The membrane fragments are centrifuged at 3000 g for 40 min and resuspended in membranes in buffer B (50 mM Tris, 25 mM $MgCl_2$, 250 mM saccharose, pH 7.4) and aliquots are stored frozen.

Binding assay is performed in a total volume of 250 µl. In each well, 75 µl buffer C (50 mM Tris, 100 mM NaCl, 1 mM EDTA, 0.1% B SA (protease free), 0.01% $NaN_3$, pH 7.4) is mixed with 50 μl {³H}-PGD₂ (at 2.5 nM (220.000 dpm per well) from Amersham, TRK734), 100 μl CRTH2 membranes to give 80 μg per well and 25 μl of test compound in buffer C containing 1% DMSO. For unspecific binding, PGD2 is added to the reaction mixture at 1 μM final concentration. This binding assay mix is incubated at it for 90 min and then filtered through a GF/C filter plate. The filter is washed three times with ice cold binding buffer. Then, 40 μl per well Microscint-40 (Packard) are added and the bound radioactivity is quantified by means of Topcourt (Packard).

Test for Antagonist Binding to the CRTH2 Receptor:

Compounds of Formula (I) display $IC_{50}$ values in the range of 0.1 nM to 1 μM, especially in the range of 1 nM to 100 nM. The following Table 13 exemplifies $IC_{50}$ values of compounds of the present invention.

TABLE 13

| Name | Binding CRTH2 $IC_{50}$ [μM] |
| --- | --- |
| [2-(Naphthalene-1-carbonyl)-1,2,3,4-tetrahydro-pyrido[4,3-b]indol-5-yl]-acetic acid | 0.012 |
| [2-(3-Chloro-benzoyl)-1,2,3,4-tetrahydro-pyrido[4,3-b]indol-5-yl]-acetic acid | 0.015 |
| [2-(2-Bromo-3-methyl-benzoyl)-1,2,3,4-tetrahydro-pyrido[4,3-b]indol-5-yl]-acetic acid | 0.014 |
| [2-(4'-Ethyl-biphenyl-4-carbonyl)-1,2,3,4-tetrahydro-pyrido[4,3-b]indol-5-yl]-acetic acid | 0.007 |
| [2-(4'-Ethyl-biphenyl-4-carbonyl)-8-fluoro-1,2,3,4-tetrahydro-pyrido[4,3-b]indol-5-yl]-acetic acid | 0.001 |
| (2-Benzoyl-8-trifluoromethyl-1,2,3,4-tetrahydro-pyrido[4,3-b]indol-5-yl)-acetic acid | 0.001 |
| [8-Fluoro-2-(2-naphthalen-1-yl-acetyl)-1,2,3,4-tetrahydro-pyrido[4,3-b]indol-5-yl]-acetic acid | 0.003 |
| [8-Bromo-2-(thiophene-2-carbonyl)-1,2,3,4-tetrahydro-pyrido[4,3-b]indol-5-yl]-acetic acid | 0.004 |
| [2-(5-Bromo-naphthalene-1-carbonyl)-1,2,3,4-tetrahydro-pyrido[4,3-b]indol-5-yl]-acetic acid | 0.012 |

Intracellular Calcium Mobilization Assay (FLIPR):

Cells (HEK-293), stably expressing the hCRTH₂ receptor under the control of the cytomegalovirus promotor from a single insertion of the expression vector pcDNA5 (Invitrogen), are grown to confluency in DMEM (low glucose, Gibco) medium supplemented with 10% fetal calf serum (both Bioconcept, Switzerland) under standard mammalian cell culture conditions (37° C. in a humidified atmosphere of 5% CO₂). Cells are detached from culture dishes using a dissociation buffer (0.02% EDTA in PBS, Gibco) for 1 min, and collected by centrifugation at 200 g at rt for 5 min in assay buffer [equal parts of Hank's BSS (HBSS, Bioconcept) and DMEM (low glucose, without phenol red, Gibco)]. After incubation for 45 min (37° C. and 5% CO₂) in the presence of 1 μM Fluo-4 and 0.04% Pluronic F-127 (both Molecular Probes), 20 mM HEPES (Gibco) in assay buffer, the cells are washed with and resuspended in assay buffer, then seeded onto 3 84-welt FLIPR assay plates (Greiner) at 50,000 cells in 66 μl per well, and sedimented by centrifugation.

Stock solutions of test compounds are made up at a concentration of 10 mM in DMSO, and serially diluted in assay buffer to concentrations required for inhibition dose response curves. Prostaglandin D₂ (Biomol, Plymouth Meeting, Pa.) is used as an agonist.

A FLIPR384 instrument (Molecular Devices) is operated according to the manufacturer's standard instructions, adding 4 μl of test compound dissolved at 10 mM in DMSO and diluted prior to the experiment in assay buffer to obtain the desired final concentration. 10 μl of 80 nM prostaglandin D₂ (Biomol, Plymouth Meeting, Pa.) in assay buffer, supplemented with 0.8% bovine serum albumin (fatty acid content<0.02%, Sigma), is then added to obtain a final concentration of 10 nM and 0.1%, respectively. Changes in fluorescence are monitored before and after the addition of test compounds at $\lambda_{ex}$=488 nm and $\lambda_{em}$=540 nm. Emission peak values above base level after prostaglandin D₂ addition are exported after base line subtraction. Values are normalized to high-level control (no test compound added) after subtraction of base line value (no prostaglandin D₂ added). The program XLlfit 3.0 (IDBS) is used to fit the data to a single site dose response curve of the equation (A+((B−A)/(1+((C/x)^D)))) and to calculate the $IC_{50}$ values.

Antagonist Analysis

Compounds of general Formula (I) antagonize prostaglandin D2 mediated hCRTH2 receptor activity with an $IC_{50}$ of less than 10 μM, especially less than 300 nM as exemplified in the following Table 14.

TABLE 14

| Name | FLIPR CRTH2 $IC_{50}$ [μM] |
| --- | --- |
| [2-(3,4,5-Trimethoxy-benzoyl)-1,2,3,4-tetrahydro-pyrido[4,3-b]indol-5-yl]-acetic acid | 0.091 |
| [2-(3-Chloro-benzoyl)-1,2,3,4-tetrahydro-pyrido[4,3-b]indol-5-yl]-acetic acid | 0.174 |
| [2-(4-Bromo-benzoyl)-1,2,3,4-tetrahydro-pyrido[4,3-b]indol-5-yl]-acetic acid | 0.083 |
| [2-(Furan-2-carbonyl)-1,2,3,4-tetrahydro-pyrido[4,3-b]indol-5-yl]-acetic acid | 0.088 |
| [8-Chloro-2-(2-methoxy-naphthalene-1-carbonyl)-1,2,3,4-tetrahydro-pyrido[4,3-b]indol-5-yl]-acetic acid | 0.003 |
| [8-Bromo-2-(2-methyl-3-methyl-benzoyl)-1,2,3,4-tetrahydro-pyrido[4,3-b]indol-5-yl]-acetic acid | 0.015 |
| [2-(1H-Indole-4-carbonyl)-1,2,3,4-tetrahydro-pyrido[4,3-b]indol-5-yl]-acetic acid | 0.019 |
| 5-Carboxymethyl-8-fluoro-1,3,4,5-tetrahydro-pyrido[4,3-b]indole-2-carboxylic acid tert-butyl ester | 0.022 |
| [8-Chloro-2-(thiophene-2-carbonyl)-1,2,3,4-tetrahydro-pyrido[4,3-b]indol-5-yl]-acetic acid | 0.050 |

The invention claimed is:

1. The compound of Formula I,

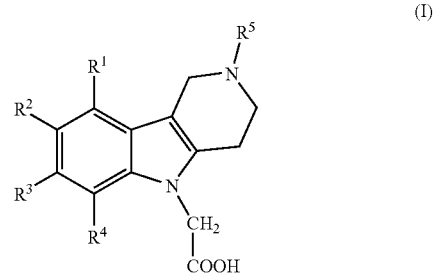

wherein
R¹, R², R³ and R⁴ independently represent hydrogen, $C_1$-$C_5$-alkyl, $C_1$-$C_5$-alkoxy, halogen, nitro, cyano or formyl; and
R⁵ represents phenyl-carbonyl or naphthyl-carbonyl, wherein the phenyl or naphthyl moiety is optionally substituted by one or more substituents selected from $C_1$-$C_5$-alkyl, $C_1$-$C_5$-alkoxy and halogen;
or a salt of the compound.

2. The compound according to claim 1, wherein $R^2$ is selected from methyl, fluoro, chloro, bromo and trifluoromethyl; $R^3$ is hydrogen or chloro; and $R^1$ and $R^4$ are both hydrogen;
or a salt of the compound.

3. The compound according to claim 1, wherein $R^5$ represents naphthyl-carbonyl, wherein the naphthyl moiety is unsubstituted or substituted by one or more substituents selected from $C_1$-$C_5$-alkyl, $C_1$-$C_5$-alkoxy and halogen;
or a salt of the compound.

4. The compound according to claim 1, wherein $R^5$ represents naphthyl-carbonyl, wherein the naphthyl moiety is unsubstituted or substituted by one or two substituents selected from $C_1$-$C_5$-alkyl, $C_1$-$C_5$-alkoxy and halogen;
or a salt of the compound.

5. The compound according to claim 4, wherein said naphthyl-carbonyl is naphthalene-1-carbonyl;
or a salt of the compound.

6. The compound according to claim 4, wherein said substituents are selected from $C_1$-$C_5$-alkoxy and halogen;
or a salt of the compound.

7. The compound according claim 4, wherein said substituents are selected from methoxy, ethoxy, and fluoro;
or a salt of the compound.

8. The compound according to claim 1, wherein $R^5$ represents phenyl-carbonyl, wherein the phenyl moiety is unsubstituted or substituted by one or two substituents selected from $C_1$-$C_5$-alkyl, $C_1$-$C_5$-alkoxy and halogen;
or a salt of the compound.

9. The compound according to claim 8, wherein said substituents are selected from $C_1$-$C_5$-alkyl and halogen;
or a salt of the compound.

10. The compound according claim 8, wherein said substituents are selected from methyl, fluoro, chloro and bromo;
or a salt of the compound.

11. The compound according claim 1, wherein the compound is [8-fluoro-2-(2-methoxy-naphthalene-1-carbonyl)-1,2,3,4-tetrahydro-pyrido[4,3-b]indol-5-yl]-acetic acid, or a salt of the compound.

12. The compound according claim 1, wherein the compound is [8-chloro-2-(4-methoxy-naphthalene-1-carbonyl)-1,2,3,4-tetrahydro-pyrido[4,3-b]indol-5-yl]-acetic acid, or a salt of the compound.

13. The compound according to claim 1, wherein the compound is [8-methyl-2-(naphthalene-1-carbonyl)-1,2,3,4-tetrahydro-pyrido[4,3-b]indol-5-yl]-acetic acid, or a salt of the compound.

14. The compound according to claim 1, wherein the compound is [8-fluoro-2-(naphthalene-1-carbonyl)-1,2,3,4-tetrahydro-pyrido[4,3-b]indol-5-yl]-acetic acid, or a salt of the compound.

15. The compound according to claim 1, wherein the compound is [8-chloro-2-(2-ethoxy-naphthalene-1-carbonyl)-1,2,3,4-tetrahydro-pyrido[4,3-b]indol-5-yl]-acetic acid, or a salt of the compound.

16. The compound according to claim 1, wherein the compound is [2-(4-fluoro-naphthalene-1-carbonyl)-1,2,3,4-tetrahydro-pyrido[4,3-b]indol-5-yl]-acetic acid, or a salt of the compound.

17. The compound according to claim 1, wherein the compound is [2-(3-chloro-benzoyl)-8-methyl-1,2,3,4-tetrahydro-pyrido[4,3-b]indol-5-yl]-acetic acid, or a salt of the compound.

18. The compound according to claim 1, wherein the compound is [2-(3-chloro-benzoyl)-8-fluoro-1,2,3,4-tetrahydro-pyrido[4,3-b]indol-5-yl]-acetic acid, or a salt of the compound.

19. The compound according to claim 1, wherein $R^1$, $R^2$, $R^3$ and $R^4$ represent hydrogen;
or a salt of the compound.

20. The compound according to claim 1, wherein one or two substituents selected from $R^1$, $R^2$, $R^3$ and $R^4$ independently represent methyl, trifluoromethyl, methoxy, fluoro, chloro or bromo;
or a salt of the compound.

21. The compound according to claim 1, wherein the compound is:
(2-benzoyl-1,2,3,4-tetrahydro-pyrido[4,3-b]indol-5-yl)-acetic acid;
[2-(3,4,5-trimethoxy-benzoyl)-1,2,3,4-tetrahydro-pyrido[4,3-b]indol-5-yl]-acetic acid;
[2-(4-methoxy-benzoyl)-1,2,3,4-tetrahydro-pyrido[4,3-b]indol-5-yl]-acetic acid;
[2-(naphthalene-1-carbonyl)-1,2,3,4-tetrahydro-pyrido[4,3-b]indol-5-yl]-acetic acid;
[2-(2-methoxy-benzoyl)-1,2,3,4-tetrahydro-pyrido[4,3-b]indol-5-yl]-acetic acid;
[2-(4-tert.-butyl-benzoyl)-1,2,3,4-tetrahydro-pyrido[4,3-b]indol-5-yl]-acetic acid;
[2-(4-chloro-benzoyl)-1,2,3,4-tetrahydro-pyrido[4,3-b]indol-5-yl]-acetic acid;
[2-(3,5-dimethoxy-benzoyl)-1,2,3,4-tetrahydro-pyrido[4,3-b]indol-5-yl]-acetic acid;
[2-(3-chloro-benzoyl)-1,2,3,4-tetrahydro-pyrido[4,3-b)]indol-5-yl]-acetic acid;
[2-(4-bromo-benzoyl)-1,2,3,4-tetrahydro-pyrido[4,3-b]indol-5-yl]-acetic acid;
(2-benzoyl-8-methoxy-1,2,3,4-tetrahydro-pyrido[4,3-b]indol-5-yl)-acetic acid;
(2-benzoyl-7-methyl-1,2,3,4-tetrahydro-pyrido[4,3-b]indol-5-yl)-acetic acid;
(2-benzoyl-8-bromo-1,2,3,4-tetrahydro-pyrido[4,3-b)]indol-5-yl)-acetic acid;
(2-benzoyl-8-methyl-1,2,3,4-tetrahydro-pyrido[4,3-b]indol-5-yl)-acetic acid;
(2-benzoyl-6-methyl-1,2,3,4-tetrahydro-pyrido[4,3-b]indol-5-yl)-acetic acid;
[2-(2-bromo-3-methyl-benzoyl)-1,2,3,4-tetrahydro-pyrido[4,3-b]indol-5-yl]-acetic acid;
[2-(2-bromo-5-methyl-benzoyl)-1,2,3,4-tetrahydro-pyrido[4,3-b]indol-5-yl]-acetic acid; or
[2-(2-ethoxy-naphthalene-1-carbonyl)-1,2,3,4-tetrahydro-pyrido[4,3-b]indol-5-yl]-acetic acid
or a salt of the compound.

22. The compound according to claim 1, wherein the compound is:
[7-chloro-2-(3-chloro-benzoyl)-1,2,3,4-tetrahydro-pyrido[4,3-b]indol-5-yl]-acetic acid;
[8-chloro-2-(3-chloro-benzoyl)-1,2,3,4-tetrahydro-pyrido[4,3-b]indol-5-yl]-acetic acid;
[6-chloro-2-(3-chloro-benzoyl)-1,2,3,4-tetrahydro-pyrido[4,3-b]indol-5-yl]-acetic acid;
[2-(3-chloro-benzoyl)-7-methyl-1,2,3,4-tetrahydro-pyrido[4,3-b]indol-5-yl]-acetic acid;
[2-(3-chloro-benzoyl)-8-methyl-1,2,3,4-tetrahydro-pyrido[4,3-b]indol-5-yl]-acetic acid;
[8-fluoro-2-(2-methoxy-naphthalene-1-carbonyl)-1,2,3,4-tetrahydro-pyrido[4,3-b]indol-5-yl]-acetic acid;
[8-fluoro-2-(4-methoxy-naphthalene-1-carbonyl)-1,2,3,4-tetrahydro-pyrido[4,3-b]indol-5-yl]-acetic acid;
[8-chloro-2-(2-methoxy-naphthalene-1-carbonyl)-1,2,3,4-tetrahydro-pyrido[4,3-b]indol-5-yl]-acetic acid;
[8-chloro-2-(4-methoxy-naphthalene-1-carbonyl)-1,2,3,4-tetrahydro-pyrido[4,3-b]indol-5-yl]-acetic acid;

[2-(2-methoxy-naphthalene-1-carbonyl)-8-methyl-1,2,3,4-tetrahydro-pyrido[4,3-b]indol-5-yl]-acetic acid;
[2-(4-methoxy-naphthalene-1-carbonyl)-8-methyl-1,2,3,4-tetrahydro-pyrido[4,3-b]indol-5-yl]-acetic acid;
2-(2-methoxy-naphthalene-1-carbonyl)-7-methyl-1,2,3,4-tetrahydro-pyrido[4,3-bit indol-5-yl]-acetic acid;
[2-(2-ethoxy-naphthalene-1-carbonyl)-8-methyl-1,2,3,4-tetrahydro-pyrido[4,3-b]indol-5-yl]-acetic acid;
[2-(2-ethoxy-naphthalene-1-carbonyl)-7-methyl-1,2,3,4-tetrahydro-pyrido[4,3-b]indol-5-yl]-acetic acid;
[2-(4-methoxy-naphthalene-1-carbonyl)-7-methyl-1,2,3,4-tetrahydro-pyrido[4,3-b]indol-5-yl]-acetic acid;
[2-(2-fluoro-benzoyl)-1,2,3,4-tetrahydro-pyrido[4,3-b]indol-5-yl]-acetic acid;
[2-(3-fluoro-benzoyl)-1,2,3,4-tetrahydro-pyrido[4,3-b]indol-5-yl]-acetic acid;
[2-(3,5-difluoro-benzoyl)-1,2,3,4-tetrahydro-pyrido[4,3-b)]indol-5-yl]-acetic acid;
[2-(3,4,5-trifluoro-benzoyl)-1,2,3,4-tetrahydro-pyrido[4,3-b]indol-5-yl]-acetic acid;
[2-(2,3,4,5-tetrafluoro-benzoyl)-1,2,3,4-tetrahydro-pyrido[4,3-b)] indol-5-yl]-acetic acid;
(2-benzoyl-8-fluoro-1,2,3,4-tetrahydro-pyrido[4,3-b]indol-5-yl)-acetic acid;
(2-benzoyl-6-chloro-1,2,3,4-tetrahydro-pyrido[4,3-b)]indol-5-yl)-acetic acid;
(2-benzoyl-8-isopropyl-1,2,3,4-tetrahydro-pyrido[4,3-b]indol-5-yl)-acetic acid;
(2-benzoyl-8-chloro-1,2,3,4-tetrahydro-pyrido[4,3-b]indol-5-yl)-acetic acid;
(2-benzoyl-7,8-dichloro-1,2,3,4-tetrahydro-pyrido[4,3-b]indol-5-yl)-acetic acid;
(2-benzoyl-8-trifluoromethyl-1,2,3,4-tetrahydro-pyrido[4,3-b]indol-5-yl)-acetic acid;
(2-benzoyl-8-tert-butyl-1,2,3,4-tetrahydro-pyrido[4,3-b]indol-5-yl)-acetic acid;
(2-benzoyl-7-chloro-8-methyl-1,2,3,4-tetrahydro-pyrido[4,3-b)]indol-5-yl)-acetic acid;
(2-benzoyl-7,8-dimethyl-1,2,3,4-tetrahydro-pyrido[4,3-b]indol-5-yl)-acetic acid;
(2-benzoyl-7-fluoro-1,2,3,4-tetrahydro-pyrido[4,3-b]indol-5-yl)-acetic acid;
[8-chloro-2-(naphthalene-1-carbonyl)-1,2,3,4-tetrahydro-pyrido[4,3-b]indol-5-yl]-acetic acid;
[6-chloro-2-(naphthalene-1-carbonyl)-1,2,3,4-tetrahydro-pyrido[4,3-b]indol-5-yl]-acetic acid;
[7-methyl-2-(naphthalene-1-carbonyl)-1,2,3,4-tetrahydro-pyrido[4,3-b]indol-5-yl]-acetic acid;
[8-methyl-2-(naphthalene-1-carbonyl)-1,2,3,4-tetrahydro-pyrido[4,3-b]indol-5-yl]-acetic acid;
[8-bromo-2-(naphthalene-1-carbonyl)-1,2,3,4-tetrahydro-pyrido[4,3-b]indol-5-yl]-acetic acid;
[8-fluoro-2-(naphthalene-1-carbonyl)-1,2,3,4-tetrahydro-pyrido[4,3-b]indol-5-yl]-acetic acid;
[2-(2-bromo-3-methyl-benzoyl)-7-chloro-1,2,3,4-tetrahydro-pyrido[4,3-b]indol-5-yl]-acetic acid;
[2-(2-bromo-3-methyl-benzoyl)-8-chloro-1,2,3,4-tetrahydro-pyrido[4,3-b)]indol-5-yl]-acetic acid;
[2-(2-bromo-3-methyl-benzoyl)-6-chloro-1,2,3,4-tetrahydro-pyrido[4,3-b]indol-5-yl]-acetic acid;
[2-(2-bromo-3-methyl-benzoyl)-7-methyl-1,2,3,4-tetrahydro-pyrido[4,3-b]indol-5-yl]-acetic acid;
[2-(2-bromo-3-methyl-benzoyl)-8-methyl-1,2,3,4-tetrahydro-pyrido[4,3-b]indol-5-yl]-acetic acid;
[2-bromo-2-(2-bromo-3-methyl-benzoyl)-1,2,3,4-tetrahydro-pyrido[4,3-b]indol-5-yl]-acetic acid;
[2-(2-bromo-3-methyl-benzoyl)-8-fluoro-1,2,3,4-tetrahydro-pyrido[4,3-b]indol-5-yl]-acetic acid;
[8-bromo-2-(2-ethoxy-naphthalene-1-carbonyl)-1,2,3,4-tetrahydro-pyrido[4,3-b]indol-5-yl]-acetic acid;
[2-(2-ethoxy-naphthalene-1-carbonyl)-8-fluoro-1,2,3,4-tetrahydro-pyrido[4,3-b]indol-5-yl]-acetic acid;
[8-chloro-2-(2-ethoxy-naphthalene-1-carbonyl)-1,2,3,4-tetrahydro-pyrido[4,3-b]indol-5-yl]-acetic acid;
[2-(4-methoxy-naphthalene-1-carbonyl)-1,2,3,4-tetrahydro-pyrido[4,3-b]indol-5-yl]-acetic acid;
[2-(5-bromo-naphthalene-1-carbonyl)-1,2,3,4-tetrahydro-pyrido[4,3-b]indol-5-yl]-acetic acid;
[2-(4-methyl-naphthalene-1-carbonyl)-1,2,3,4-tetrahydro-pyrido[4,3-b]indol-5-yl]-acetic acid;
[2-(2-methyl-naphthalene-1-carbonyl)-1,2,3,4-tetrahydro-pyrido[4,3-b]indol-5-yl]-acetic acid;
[2-(4-fluoro-naphthalene-1-carbonyl)-1,2,3,4-tetrahydro-pyrido[4,3-b]indol-5-yl]-acetic acid;
[2-(2-methoxy-naphthalene-1-carbonyl)-1,2,3,4-tetrahydro-pyrido[4,3-b]indol-5-yl]-acetic acid; or
[2-(2,4,6-trifluoro-benzoyl)-1,2,3,4-tetrahydro-pyrido[4,3-b]indol-5-yl]-acetic acid
or a salt of the compound.

23. A pharmaceutical composition comprising at least one compound according to any one of claims 21, 22, 1, 11, 12, 13, 14, 15, 16, 17, or 18, or a salt of the compound, and an inert carrier material and/or adjuvant.

24. A method of antagonizing prostaglandin D2 mediated hCRTH2 receptor activity, comprising administering to a subject in need thereof an effective amount of the compound according to any one of claims 21, 22, 1, 11, 12, 13, 14, 15, 16, 17, or 18, or a salt of the compound.

25. The method of claim 24, wherein the subject suffers from allergic asthma, rhinitis, allergic nephritis, conjunctivitis, atopic dermatitis, bronchial asthma, food allergy, anaphylactic shock, urticaria, eczema, itching, Churg-Strauss syndrome, or sinusitis.

* * * * *